(12) United States Patent
Barrett et al.

(10) Patent No.: US 11,804,303 B2
(45) Date of Patent: Oct. 31, 2023

(54) EVALUATION OF RESPIRATORY DISEASE RISK IN A GEOGRAPHIC REGION BASED ON MEDICAMENT DEVICE MONITORING

(71) Applicant: Reciprocal Labs Corporation, Madison, WI (US)

(72) Inventors: Meredith A. Barrett, Redwood City, CA (US); Michael J. Tuffli, Kentfield, CA (US); Michael Lohmeier, Sun Prairie, WI (US); Robert Austin Lee, San Francisco, CA (US); Christopher Hogg, San Francisco, CA (US); John David Van Sickle, Oregon, WI (US); Gregory F. Tracy, Madison, WI (US); Nicholas John Hirons, Oakland, CA (US)

(73) Assignee: Reciprocal Labs Corporation, Madison, WI (US)

( * ) Notice: Subject to any disclaimer, the term of this patent is extended or adjusted under 35 U.S.C. 154(b) by 0 days.

(21) Appl. No.: 16/290,820

(22) Filed: Mar. 1, 2019

(65) Prior Publication Data

US 2019/0272925 A1 Sep. 5, 2019

Related U.S. Application Data

(60) Provisional application No. 62/637,300, filed on Mar. 1, 2018.

(51) Int. Cl.
*G16H 50/30* (2018.01)
*G16H 50/80* (2018.01)
*G16H 10/20* (2018.01)

(52) U.S. Cl.
CPC ............. *G16H 50/30* (2018.01); *G16H 50/80* (2018.01); *G16H 10/20* (2018.01)

(58) Field of Classification Search
CPC ...... G16H 50/30; G16H 50/80; A63B 220/62; A63F 2009/0656; A63F 2300/535;
(Continued)

(56) References Cited

U.S. PATENT DOCUMENTS 5,284,133 A 2/1994 Burns et al.
5,363,842 A 11/1994 Mishelevich et al.
(Continued)

FOREIGN PATENT DOCUMENTS

AU 2017/200452 * 1/2017
WO 2015/0178907 A1 11/2015

OTHER PUBLICATIONS

J. Su, et.al., "Feasibility of Deploying Inhaler Sensors To Identify The Impacts of Environmental Triggers And Built Environmental Factors On Asthma Short—Acting Bronchodilator Use", Environmental Health Perspectives, (2017), vol. 125, No. 2: pp. 254-261). (Year: 2017).*

(Continued)

*Primary Examiner* — Mamon Obeid
*Assistant Examiner* — Alaaeldin M Elshaer
(74) *Attorney, Agent, or Firm* — McDermott Will & Emery LLP

(57) ABSTRACT

A respiratory disease analytics system provides respiratory disease risk reports to a patient, provider, or third-party entity describing a patient's risk of experiencing a medication usage event given data in a geographic region. Regional data, including air pollutant conditions, weather conditions, demographic information, built environment factors, and regional health conditions for a geographic region are accessed from other sources and assigned based on event data recorded during a medicament usage event, as collected by sensors associated with the patient's medicament device/s. The regional data is assigned to medicament usage events (Continued)

occurring within a period of time. The assigned regional data is analyzed to determine an expected number of medication usage events for the geographic region occurring over the period of time.

27 Claims, 11 Drawing Sheets

(58) Field of Classification Search
CPC ........ A47K 2010/3226; A61M 1/1603; A61M 15/00; A61M 16/00; A61F 2005/0023; G06F 19/00; G06F 17/30; G06F 17/18; G06N 99/00; A61B 5/00; A61B 5/145
USPC .......................................................... 705/2, 3
See application file for complete search history.

(56) References Cited

U.S. PATENT DOCUMENTS

| | | |
|---|---|---|
| 5,477,849 A | 12/1995 | Fry |
| 5,505,192 A | 4/1996 | Samiotes et al. |
| 5,544,647 A | 8/1996 | Jewett et al. |
| 5,622,163 A | 4/1997 | Jewett et al. |
| 5,809,997 A | 9/1998 | Wolf |
| 5,976,082 A | 11/1999 | Wong et al. |
| 6,076,521 A | 6/2000 | Lindahl et al. |
| 6,190,326 B1 | 2/2001 | McKinnon et al. |
| 6,202,642 B1 | 3/2001 | McKinnon et al. |
| 6,540,672 B1 | 4/2003 | Simonsen et al. |
| 6,579,231 B1 | 6/2003 | Phipps |
| 6,637,430 B1 | 10/2003 | Voges et al. |
| 6,652,455 B1 | 11/2003 | Kocher |
| 6,729,327 B2 | 5/2004 | McFarland, Jr. |
| 6,743,202 B2 | 6/2004 | Hirschman et al. |
| 6,747,556 B2 | 6/2004 | Medema et al. |
| 6,804,558 B2 | 10/2004 | Haller et al. |
| 6,937,150 B2 | 8/2005 | Medema et al. |
| 6,958,691 B1 | 10/2005 | Anderson et al. |
| 7,151,456 B2 | 12/2006 | Godfrey |
| 7,191,777 B2 | 3/2007 | Brand et al. |
| 7,481,213 B2 | 1/2009 | Childers |
| 7,537,005 B2 | 5/2009 | Dave |
| 7,766,012 B2 | 8/2010 | Scheuch et al. |
| 8,807,131 B1 | 8/2014 | Tunnell et al. |
| 10,019,555 B2 | 7/2018 | Manice |
| 2002/0073196 A1 | 6/2002 | Westervelt |
| 2003/0098022 A1 | 5/2003 | Nakao et al. |
| 2003/0221687 A1 | 12/2003 | Kaigler |
| 2004/0148199 A1 | 7/2004 | Dixon |
| 2004/0199056 A1 | 10/2004 | Husemann et al. |
| 2004/0255936 A1 | 12/2004 | Urbanus |
| 2005/0021286 A1 | 1/2005 | Kunce |
| 2005/0172658 A1 | 1/2005 | Singer et al. |
| 2005/0028815 A1 | 2/2005 | Deaton et al. |
| 2005/0086256 A1 | 4/2005 | Owens |
| 2005/0150488 A1 | 7/2005 | Dave |
| 2005/0247312 A1 | 11/2005 | Davies |
| 2006/0089545 A1 | 4/2006 | Ratjen et al. |
| 2006/0231109 A1 | 10/2006 | Howell et al. |
| 2006/0237001 A1 | 10/2006 | Stangl |
| 2006/0237002 A1 | 10/2006 | Bonny et al. |
| 2006/0254581 A1 | 11/2006 | Genova et al. |
| 2007/0023034 A1 | 2/2007 | Jongejan et al. |
| 2007/0186923 A1 | 8/2007 | Poutiatine et al. |
| 2007/0271298 A1 | 11/2007 | Juang et al. |
| 2008/0125724 A1 | 5/2008 | Monroe |
| 2008/0201169 A1 | 8/2008 | Galasso et al. |
| 2008/0281636 A1 | 11/2008 | Jung et al. |
| 2009/0128330 A1 | 5/2009 | Monroe |
| 2009/0194104 A1 | 8/2009 | Van Sickle et al. |
| 2009/0326861 A1 | 12/2009 | Langford et al. |
| 2010/0094099 A1 | 4/2010 | Levy et al. |
| 2010/0192948 A1 | 8/2010 | Sutherland et al. |
| 2010/0252036 A1 | 10/2010 | Sutherland et al. |
| 2011/0043357 A1 | 2/2011 | Peatfield et al. |
| 2011/0253139 A1 | 10/2011 | Guthrie et al. |
| 2011/0282173 A1 | 11/2011 | Fonduca et al. |
| 2011/0290256 A1 | 12/2011 | Sather et al. |
| 2012/0055472 A1 | 3/2012 | Brunnberg et al. |
| 2014/0243749 A1 | 8/2014 | Edwards et al. |
| 2015/0335834 A1* | 11/2015 | Anandhakrishnan .. G16H 20/13 128/203.12 |
| 2016/0314256 A1* | 4/2016 | Su et al. |
| 2016/0144141 A1 | 5/2016 | Biswas et al. |
| 2016/0325057 A1 | 11/2016 | Morrison et al. |
| 2017/0224939 A1 | 8/2017 | Anderson et al. |
| 2019/0147071 A1* | 5/2019 | Shapiro .............. G06K 9/00536 707/736 |

OTHER PUBLICATIONS

J. Su, et.al., "Feasibility of Deploying Inhaler Sensors To Identify The Impacts of Environmental Triggers And Built Environmental Factors On Asthma Short—Acting Bronchodilator Use", Environmental Health Perspectives, (2017), vol. 125, No. 2: pp. 254-261), Supplemental Material. (Year: 2017).*

National Heart, Lung, and Blood Institute. Expert Panel Report 3: Guidelines for the Diagnosis and Management of Asthma Full Report 2007. United States.

Centers for Disease Control and Prevention. Surveillance for Asthma—United States, 1980-2004. Morbidity and Mortality Weekly Report (MMWR). Oct. 19, 2007; 56($S-8):1-60.

Bateman ED, et al. Can guideline-defined asthma control be achieved? The Gaining Optimal Asthma Control study. Am J Respir Crit Care Med. Oct. 1, 20045;170(8):836-44. US.

Nathan RA, et al. Development of the asthma control test: a survey for assessing asthma control. J Allergy Clin Immunol. Jan. 2004; 113(1):59-65. United States.

Frey, Complexity of chronic asthma and chronic obstructive pulmonary disease: implications for risk assessment, and disease progression and control. Lancet. 2008;372(9643).

US/RO—PCT International Search Report and Written Opinion, PCT Application No. PCT/US14/139014, dated Oct. 23, 2014, 16 pages.

US/RO—PCT International Search Report and Written Opinion, PCT Application No. PCT/US10/20055, dated May 25, 2010, 9 pages.

* cited by examiner

EVALUATION OF RESPIRATORY DISEASE RISK IN A GEOGRAPHIC REGION BASED ON MEDICAMENT DEVICE MONITORING

CROSS REFERENCE TO RELATED APPLICATIONS

This application claims the benefit of U.S. Provisional Application No. 62/637,300 filed on Mar. 1, 2018 which is incorporated herein by reference in their entirety for all purposes.

BACKGROUND

Field of Art

The disclosure relates generally to methods of improving treatment for patients who use inhalers, and more specifically to determining a regional risk of respiratory disease-related rescue events.

Description of the Related Art

Respiratory diseases remain a significant and costly public health problem. Worldwide, the World Health Organization (WHO) estimates the population with asthma may be 300 million, and predicts that it will rise to 400 million by 2025. For chronic obstructive disease (COPD), the WHO estimates 251 million people had the disease in 2016. In the United States, asthma affects 1 in 13 individuals and prevalence is on the rise, leading to more than $56 billion per year in health care utilization costs.

Despite the development of new medications, rates of hospitalizations and emergency room visits related to respiratory disease have not declined. Each year in the United States, asthma causes approximately 2 million emergency department visits, 500,000 hospitalizations, and 5,000 deaths. In addition, asthma is responsible for an estimated 15 million missed days of school, and 12 million days of work. Total annual costs to U.S. health insurers and employers are greater than $18 billion. COPD affects over 19% of individuals in the US over 65, and has emerged as the third-leading cause of death in the US. Globally, COPD is attributed with 3.17 million deaths, or 5% of all mortality globally in 2016. Over 60% of patients report that COPD symptoms adversely affect their quality of life, and cause them to lose up to 18.7 work days per year.

Air pollution has been shown to exacerbate respiratory disease morbidity and global mortality; however, previous studies have relied on aggregated, infrequently reported, or self-reported health outcomes and respiratory disease symptom data. Furthermore, previous studies often used an individual's residential address in defining the location of air pollution exposure, leading to the potential for substantial exposure misclassification. Additionally, the impact of air pollution on respiratory diseases has largely been assessed using single pollutant modeling approaches. However, patients are often exposed to multiple pollutants, and these pollutants combined with weather factors may simultaneously influence respiratory disease symptoms.

SUMMARY

A respiratory disease analytics system is a unified platform for treating, monitoring, and managing rescue events resulting from respiratory diseases. The respiratory disease analytics system tracks respiratory disease rescue medication events by receiving event notifications from a sensor attached to a medicament device (e.g., inhaler) used by a patient who has authorized the respiratory disease analytics system to help manage their respiratory disease. The sensor, when attached to or incorporated in a metered dose inhaler or other medicament device, accesses the geographical location of a client device associated with the inhaler, time, and date of the rescue usage event, and communicates that information to the respiratory disease analytics system. The respiratory disease analytics system analyzes the received events (both the most recent and previously received events) and regional data characterizing the geographic region within which the events occurred in real-time or near real-time, and delivers a risk assessment of the region.

A risk assessment is determined using a combination of regional parameters characterizing the geographic region at a given point in time including air pollutant conditions, weather conditions, local demographics, built environment factors, and health conditions describing a population within the region. The relationship between these parameters and the risk assessment generated for the patient or region is embodied by a machine-learned model that receives interpolated data. The model, and system more generally, is capable of receiving parameter values to determine an expected medicament usage for an average patient during a specified period of time. By ingesting information about the regional data within the geographic region, the respiratory disease analytics system helps prevent the occurrence of future respiratory disease medicament usage events by informing patients of the risk assessment, for example via a respiratory disease risk map. This facilitates better management of a patient's respiratory disease or respiratory disease-related illness and improves recognition of specific regions that precipitate rescue events so that the patient may avoid or accommodate these regions. The risk map may also inform health care providers or municipal decision makers about the regional risks associated with respiratory disease.

According to an embodiment, a method for determining a patient's risk of a respiratory disease medicament usage event of a geographic region includes accessing a set of medicament usage events occurring within the geographic region. The set of events were previously detected by an attachment associated with an inhaler unit which provided a rescue medication to the patient during each event. The set of events are previously detected using an attachment associated with an inhaler unit which provided a rescue medication to the patient as part of each of the events. Each usage event is assigned a time stamp during which the usage event occurred and a geographic label identifying the geographic region where the event occurred. The method also includes identifying, based on the geographic label and the time stamp, one or more environmental, demographic, built environment, and health parameters that affect medicament usage events in the geographic region. The system assigns the identified environmental, demographic, built environment, and health parameter values, to each medicament usage event occurring over a previous time period, wherein each parameter value is assigned based on the timestamp recorded by the medicament usage event. Additionally, the system inputs the parameter values assigned to medicament usage event into a function to determine an expected number of medicament usage events for the geographic region during the time period and determines a risk assessment based on the expected number of medicament usage events. In response to determining the risk assessment, the system sends a risk report to a patient, provider, or third-party entity containing information describing the risk assessment for the geographic region.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. System Environment

Figure 1:
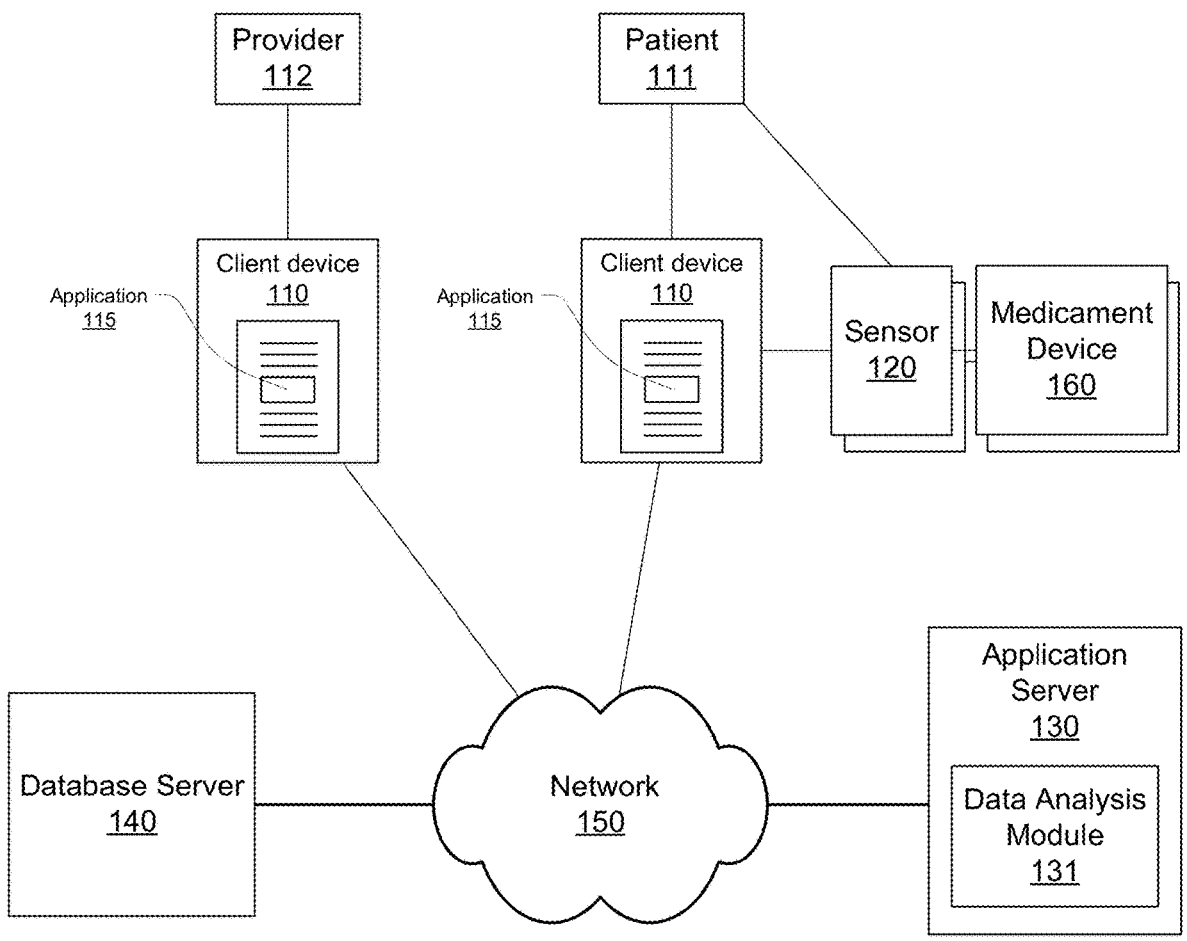
FIG. 1 shows a respiratory disease analytics system for monitoring accurate, real-time medicament device usage, performing analytics on that data, and providing respiratory disease rescue event risk reports, according to one embodiment.

FIG. 1 shows a respiratory disease analytics system 100 for monitoring accurate, real-time medicament device events, performing analytics on that data, and providing respiratory disease rescue event risk reports, according to one embodiment.

The respiratory disease analytics system includes client computing devices 110, a medicament device sensor 120, a medicament device 160, an application server 130, database server 140, and a network 150. Although FIG. 1 illustrates only a single instance of most of the components of the respiratory disease analytics system 100, in practice more than one of each component may be present, and additional or fewer components may be used.

I.A. Client Device and Application

The client devices 110, at the behest of their users, interact with the respiratory disease analytics system 100 via the network 150. For purposes of explanation and clarity it is useful to identify at least two different types of users. A patient 111 is a user burdened with a respiratory disease who makes use of the respiratory disease analytics system 100 at least in part to obtain personalized asthma rescue event risk reports provided by the server 130 and asthma management notifications created by their health care provider 112. Such reports can be provided in exchange for the user's permission to allow the asthma analytics system 100 to monitor the patient's 111 medicament device 160 usage. As will be explained below, medication events are detected by a sensor 120 associated with the medicament device 160 and the user's client device 100, which in turn reports to the application server 130, which in turn can initiate a process to generate risk reports which are provided to the user through the client device 110.

Another type of user is a healthcare provider 112 who, again with the patient's 111 express permission, also receives reports regarding a patient's respiratory disease management, as well as aggregated respiratory disease community rescue event data and derived statistics regarding respiratory disease events and other associated data. Other types of users are also contemplated, such as parents/ guardians of patients 111 who may also want to receive reports in the event that their own client devices 110 are distinct from that of their children.

The client device 110 is a computer system. An example physical implementation is described more completely below with respect to FIG. 2. The client device 110 is configured to wirelessly communicate with the respiratory disease analytics system 100 via network 150. With network 150 access, the client device 110 transmits to application server 130 the user's geographical location and the time of a rescue medication event, as well as information describing the event as received from the associated medicament device sensor 120 (referred to throughout as "sensor 120").

Regarding user location and event times, the client device 110 may determine the geographical location and time of a rescue event through use of information about the cellular or wireless network 150 to which it is connected. For example, the current geographical location of the client device 110 may be determined by directly querying the software stack providing the network 150 connection. Alternatively, the geographical location information may be obtained by pinging an external web service (not shown in FIG. 1) made accessible via network 150. The time of an event can be provided by the sensor 120 as part of the event data or added to event data by querying an appropriate software routine available as part of the client device's native operating system.

In addition to communicating with the application server 130, client devices 110 connected wirelessly to the application server 130 may also exchange information with other connected client devices 110. For example, through a client software application 115, a healthcare provider 112 may receive a risk exacerbation report describing a recent rescue event about a patient 111, then in response send a recommendation to the patient 111 for post-respiratory disease rescue event treatment. Similarly, through application 115 patients 111 may communicate with their health care providers 112 and other patients 111.

The application 115 provides a user interface (herein referred to as a "dashboard") that is displayed on a screen of the client device 110 and allows a user to input commands to control the operation of the application 115. The dashboard is the mechanism by which healthcare providers 112 and patients 111 access the respiratory disease analytics system 100. For example, the dashboard allows patients 111 and providers 112 to interact with each other, receive respiratory disease rescue event risk reports, exchange messages about treatment, provide and receive additional event and non-event data, and so on. The application 115 may be coded as a web page, series of web pages, or content otherwise coded to render within an internet browser. The application 115 may also be coded as a proprietary application configured to operate on the native operating system of the client device 110. The dashboard is more completely described below in conjunction with FIG. 3.

In addition to providing the dashboard, the application 115 may also perform some data processing on respiratory disease rescue event data locally using the resources of client device 110 before sending the processed data through the network 150. Event data sent through the network 110 is received by the application server 130 where it is analyzed and processed for storage and retrieval in conjunction with database server 140. The application server 130 may direct retrieval and storage request to the database system 130 as required by the client application 115.

The client device 110 communicates with the sensor 120 using a network adapter and either a wired or wireless communication protocol, an example of which is the Bluetooth Low Energy (BTLE) protocol. BTLE is a short-ranged, low-powered, protocol standard that transmits data wirelessly over radio links in short range wireless networks. After the sensor 120 and client device 110 have been paired with each other using a BTLE passkey, the sensor 120 automatically synchronizes and communicates information relating to medicament device usage with the client device 110. If the sensor 120 has not been paired with a client device 110 prior to a rescue medication event, the information is stored locally by the sensor 120 until such a pairing occurs. Upon pairing, the sensor 120 communicates any stored event records to the client device 110. In other implementations, other types of wireless connections are used (e.g., infrared or 802.11).

Although client devices 110 and medicament devices 160 are described above as being separate physical devices (such as smart phones and inhalers, respectively), the medicament devices 160 may include not only sensors 120 integrated into a single housing with the device 160, but also aspects of the client device 110. For example, a medicament device 160 may include an audiovisual interface including a display or other lighting elements as well as speakers for presenting visual and audible information. In such an implementation, the medicament device 160 itself may present the contents of reports provided by the server 130 directly, in place of or in addition to presenting them through the client devices 110.

I.B. Medicament Device and Sensor

The medicament device 160 is a medical device used to deliver medication to a patient (i.e., rescue medication to the lungs of a user experiencing constricted respiratory airflow or controller medication as prescribed for a patient). Medicament devices (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers include a pressured propellant canister of aerosol medicine, a metering valve for delivering a regulated medicine dosage amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline.

Each patient may be associated with more than one medicament device 160. For example, the patient may have a rescue medicament device 160 that dispenses rescue medication, and a controller medicament device 160 that dispenses controller medication. Similarly, each patient may be associated with more than one sensor 120, each chosen to operate with one of the patient's medicament devices 160.

Generally, a sensor 120 is a physical device that monitors the usage of the medicament dispenser 160. The sensor 120 is either removably attachable to the medicament dispenser without impeding the operation of the medication dispenser, or the sensor 120 is an integrated component that is a native part of the medicament dispenser 160 as made available by its manufacturer.

The sensor 120 includes its own network adapter (not shown) that communicates with the client device 110 either through a wired connection, or more typically through a wireless radio frequency connection. In one embodiment, the network adapter is a Bluetooth Low Energy (BTLE) wireless transmitter. However, in other embodiments, other types of wireless communication may be used (e.g., infrared, 802.11).

The sensor 120 may also be configured to communicate more directly with the application server 130. For example, if the network adapter of the sensor 120 is configured to communicate via a wireless standard such as 802.11 or LTE, the adapter may exchange data with a wireless access point such as a wireless router, which may in turn communicate with the application server 130 without necessarily involving the client device 110 in every exchange of data. These two methods of communicating are not mutually exclusive, and the sensor 120 may be configured to communicate with both the client device 110 and the application server 130, for example using redundant transmission to ensure event data arrives at the application server 130 or to provide information directly to the client device 110 while the application server 130 is determining what report to provide in response to an event.

As introduced above, the sensor 120 captures data about usage of the medicament device 160. Specifically, each sensor 120 is configured to capture the date, the time, and geographical location of the rescue medication event, that is, usages of the rescue medicament device 160, by the patient 111. Each sensor 120 transmits the event data in real-time or as soon as a network connection is achieved, automatically without input from the patient 111 or health care provider 112, thereby offering an immediate objective signal of respiratory disease symptoms in real-time and precise estimation of ambient air pollution exposures, for example down to a minute and a −5-meter resolution. The medication event information is sent to the application server 130 for use in analysis, generation of respiratory disease rescue event reports, and in aggregate analyses of event data across multiple patients. Accordingly, when aggregated across a community, the data collected by a sensor 120 may supplement traditional respiratory health surveillance and provide insight to policy-making aimed at reducing respiratory disease morbidity.

In some embodiments, the sensor 120 receives data from third party services at periodic time intervals, for example air pollution data recorded by Environmental Protection Agency (EPA), weather data recorded by the Quality Controlled Local Climatological Data Repository (QCLCD) or the National Oceanic and Atmospheric Administration (NOAA), and census or demographic data recorded by a government agency. The sensor 120 may communicates a first "heartbeat" signal to the application server when a medicament usage event is detected. In response, the application server 130 communicates a second heartbeat signal to one or more third party servers to access data from the servers at periodic time intervals.

In some embodiments, determining a risk analysis for a geographic region may be determined during each heartbeat such that the analysis reflects the most accurate regional data. In some embodiments, the heartbeat reports sensor battery life to the server and confirms no medicament usage events have occurred since the last heartbeat was received. In one implementation, the heartbeat occurs approximately every three hours, depending on usage and battery life. In alternate embodiments, the set of heartbeats occur at a frequency based on the availability of updated region parameter data. Region parameters are further described with reference to FIG. 6.

To accomplish this goal, there are a number of different ways for the sensor 120 to be constructed, and in part the construction will depend upon the construction of the medicament device itself 160. Generally, all sensors 120 will include an onboard processor, persistent memory, and the network adapter mentioned above that together function to record, store, and report medication event information to the client device 110 and/or server 130. Sensors 120 may also include a clock for recording the time and date of events.

Regarding specific sensor 120 constructions, traditional inhalers, such as mechanical dose counters, are not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry that may report event information as an electrical data signal which a sensor 120 is designed to receive and interpret. For example, the medicament device 160 itself may report movement, priming, and activation to the sensor 120. In one embodiment, the sensor detects movement of the medicament device, for example an opening in the medicament cover which indicates that medication is being dispensed. In alternate embodiments, the sensor may detect movement of the canister to a position from which medication is dispensed. After detecting such movements which indicate that the medicament device has been activated, the sensor may report that the medicament device has dispensed medication and the time at which it dispensed the medication.

More information regarding hardware and software components for the sensors 120 and medicament devices 160, as well as the interaction between them to record rescue medication events can be found in U.S. patent application Ser. No. 12/348,424, filed Jan. 1, 2009, and International Application No. PCT/US2014/039014, filed May 21, 2014, both of which are incorporated by reference herein in their entirety.

I.C. Application Server

Figure 2:
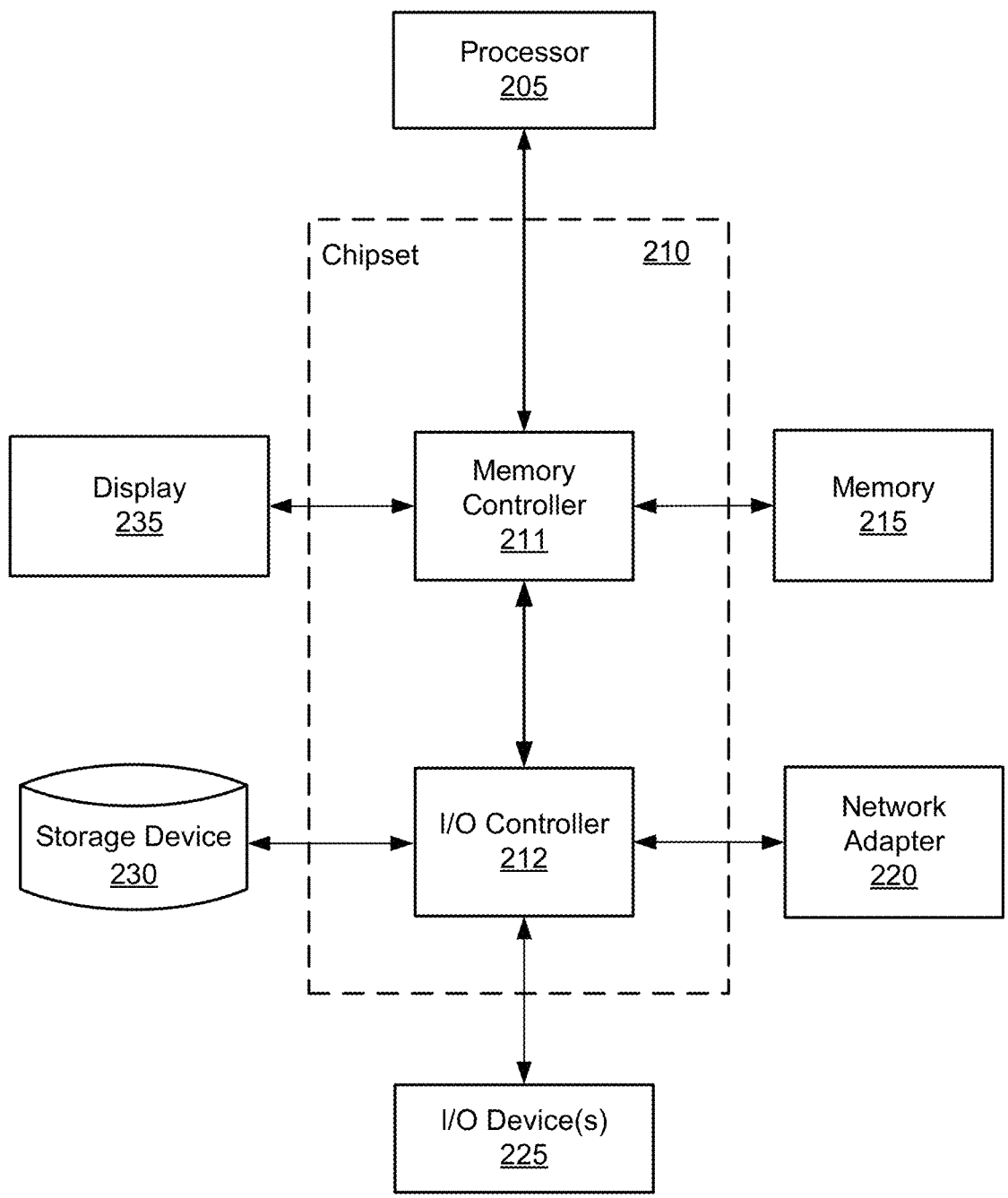
FIG. 2 is a high-level block diagram illustrating an example of a computing device used in either as a client device, application server, and/or database server, according to one embodiment.

The application server 130 is a computer or network of computers. Although a simplified example is illustrated in FIG. 2, typically the application server 130 will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data such as the asthma reports contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use respiratory disease analytics system 100 by many different client devices 110 through network 150, and thus at a high level can be generally characterized as a cloud-based system. The application server 130 generally provides a platform for patients 111 and healthcare providers 112 to report data recorded by the sensors associated with their medicament devices 160 including both rescue medication and controller medication events, collaborate on respiratory disease treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the respiratory disease analytics system 100. The patient profile may include identify information about the patient such as age, gender, race, smoking history, current rescue medication, current controller medication, notification preferences, a controller medication adherence plan, a patients relevant medical history such as other comorbidities, and a list of non-patient users authorized to access to the patient profile. The profile may further specify a device identifier, such as a unique media access control (MAC) address identifying the one or more client devices 110 or sensors 120 authorized to submit data (such as controller and rescue medication events) for the patient.

The profile may specify which different types of notifications are provided to patients 111 and their personal healthcare providers 112, as well as the frequency with which notifications are provided. For example, a patient 111 may authorize a healthcare provider 112 to receive notifications indicating a rescue event. The patient 111 may also authorize their healthcare provider 112 to be given access to their patient profile and rescue event history. If the healthcare provider 112 is provided access to the patient profile of the patient 111, the healthcare provider may specify controller adherence or rescue medication plans. Medication plans may include a prescribed number of doses per day for controller medications.

The application server 130 also creates profiles for health care providers 112. A health care provider profile may include identifying information about the health care provider 112, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) over by time period (e.g., weekly, monthly, yearly).

The application server 130 receives rescue medication event information from the client device 110 or the sensor 120, triggering a variety of routines on the application server 130. In the example implementations described below, the data analysis module 131 executes routines to access respiratory disease event data as well as other data including a patient's profile, analyze the data, and output the results of its analysis to both patients 111 and providers 112. The data analysis module 131 analyses the variety of data collected by the system to perform risk analyses for patients in response to a medicament usage event or a heartbeat updating one or more parameters associated with a patient. This process is generally referred to as a respiratory disease risk analysis. The respiratory disease risk analysis may be performed at any point in time, in response to a rescue event, due to a relevant change in the patient's environment, and in response to any one of a number of triggering conditions discussed further below.

Other analyses are also possible. For example, a risk assessment may be performed on rescue and controller medication use for multiple patients to identify based on spatial/temporal clusters (or outbreaks) of medication use based on historically significant permutations from individual, geographic, clinical, epidemiologic, demographic, or spatial or temporal baselines or predicted or expected values. Other types of analyses may include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations.

Responsive to any analyses performed, the application server 130 prepares and delivers push notifications to send to patients 111, authorized healthcare providers 112, and/or other users provided access to the patient's profile. Notifications can provide details about the timing, location, and affected patient(s) 111 involved in a medication rescue event. Notifications may additionally comprise a distress or emergency signal that requests emergency assistance that are distributed to emergency assistance providers 112. Notifications may also include the results of the respiratory disease risk analysis performed by the data analysis module 131. More information regarding the types of notifications that may be sent and the content they may contain is further described below.

In addition to providing push notifications in response to a respiratory disease risk analysis, notifications may also be provided as pull notifications, at particular time intervals. Additionally, some notifications (whether push or pull) may be triggered not in response to a respiratory disease risk analysis performed in response to a rescue medication event, but instead in response to a risk analysis performed in response to one of the underlying factors in the respiratory disease risk analysis changing, such that an updated notification is warranted. For example, if weather conditions indicate that an increase in air pollution is occurring or is imminent, this may trigger the carrying out of respiratory disease risk analyses for all patients located in the particular geographic area where the pollution is occurring.

Notifications are provided through the network 150 to client applications 115 in a data format specifically designed for use with the client applications, and additionally or alternatively may be provided as short message service (SMS) messages, emails, phone calls, or in other data formats communicated using other communication mediums.

I.D. Database Server

The database server 140 stores patient and provider data related data such as profiles, medication events, patient medical history (e.g., electronic medical records). Patient and provider data is encrypted for security and is at least password protected and otherwise secured to meet all Health Insurance Portability and Accountability Act (HIPAA) requirements. Any analyses (e.g., respiratory disease risk analyses) that incorporate data from multiple patients (e.g., aggregate rescue medication event data) and are provided to users is de-identified so that personally identifying information is removed to protect patient privacy.

The database server 140 also stores non-patient data used in respiratory disease risk analyses. This data includes regional data about a number of geographic regions such as public spaces in residential or commercial zones where patients are physically located and may be exposed to pollutants. This data may specifically include or be processed to obtain a patient's proximity to green space (areas including concentrated numbers of trees and plants). One example of regional data includes georeferenced weather data, such as temperature, wind patterns, humidity, and so on. Another example is georeferenced pollution data, including particulate counts and concentrations for various pollutants at an instance of time or measured empirically. All of the items of data above may vary over time, and as such the data itself may be indexed by time, for example separate data points may be available by time of day (including by minute or hour), or over longer periods such as by day, week, month, or season. Although the database server 140 is illustrated in FIG. 1 as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

Figure 6:
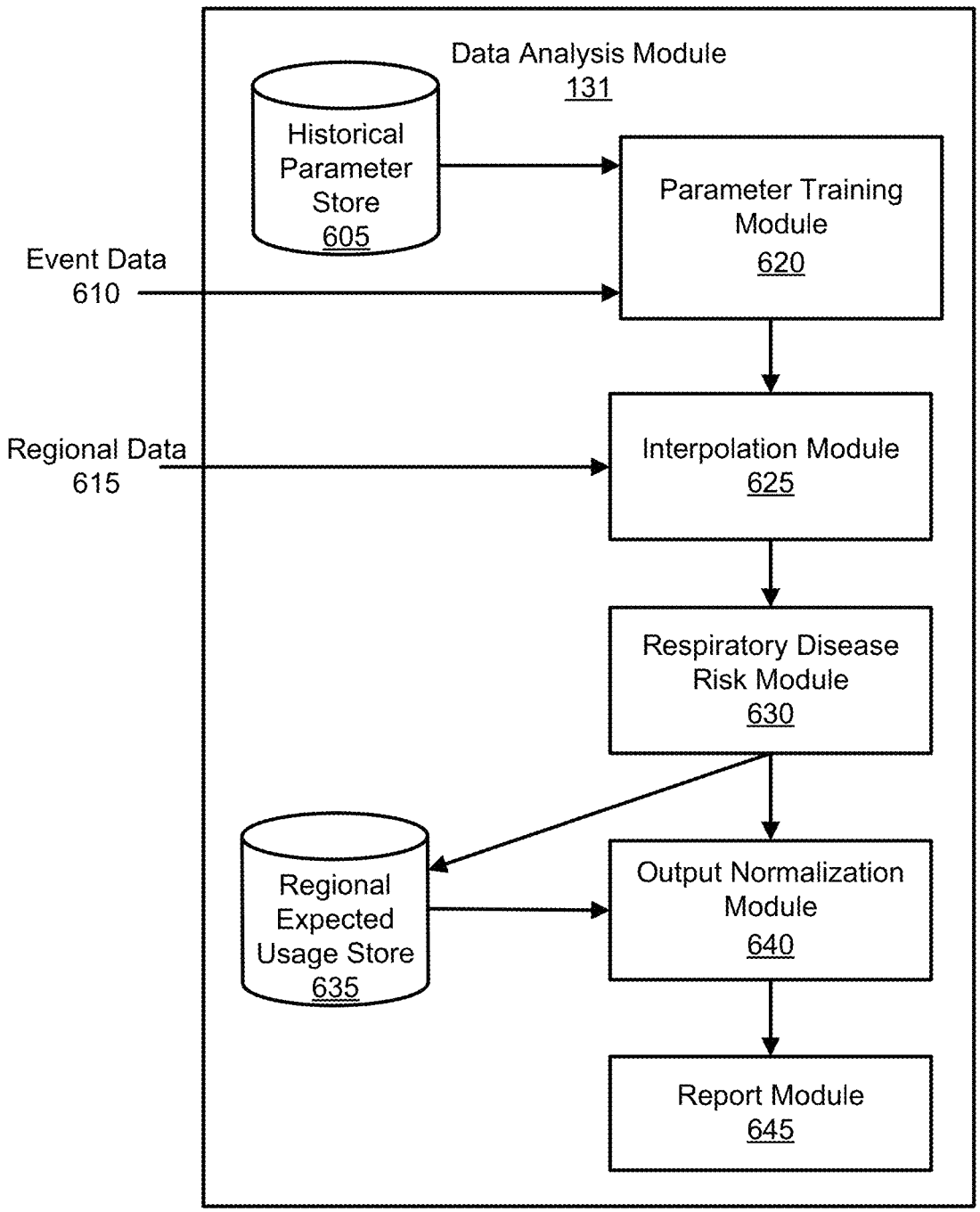
FIG. 6 is a block diagram illustrating the logical components that carry out the functions of the data analysis module, according to one embodiment.

With respect to the description of FIG. 6 below, the contents of the databases described with respect to those figures may be stored in databases physically proximate to the application server 130 and separate from database server 140 as illustrated. Alternatively, those databases may be a part of database server 140, in contrast to the description of FIG. 6 illustrating them as being within data analysis module 131. This and other variations thereupon are within the scope of this description.

I.E. Network

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)).

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the respiratory disease risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Dashboard

Figure 3:
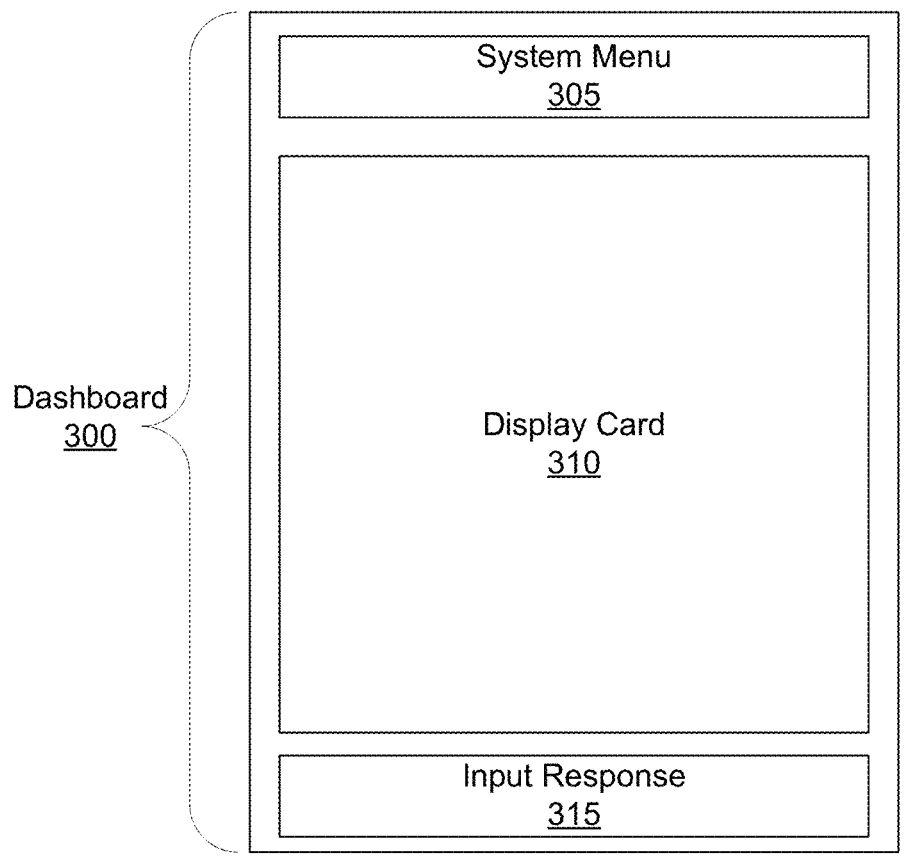
FIG. 3 shows a dashboard of a client application that allows a user to interact with a respiratory disease analytics system, according to one embodiment.

The dashboard, for example dashboard 300 illustrated in FIG. 3, allows users to interact with the respiratory disease analytics system 100. The dashboard 300 provides a means to transfer information on a user-to-user (e.g., patient 111 to provider 112) or user-to-system/system-to-user basis. Dashboards 300 are accessed through the client application 115 on the client device 110 and provide a mechanism for both patients and healthcare providers to monitor medication rescue events, exchange personalized patient healthcare information, and receive notifications such as respiratory disease rescue event risk notifications. Patients may communicate with other health care providers and other patients through the dashboard 300, for example, to discuss and share information about respiratory disease, medication usage, or respiratory disease management. The ability to share respiratory disease healthcare information may give patients or healthcare care providers experiencing a similar issue a way to share individual perspectives.

The dashboard 300 also allows authorized health care providers 112 to access a list of patients to view, annotate, update, interact with, and export information about respiratory disease patient and community data and statistics in various demographics or geographic segments. Using the dashboard 300, healthcare providers are able to monitor patients individually or in aggregate, to receive and provide feedback on how their associated patient populations are responding to respiratory disease management guidance. A healthcare provider who has access to individual or multiple patients has the ability to establish notification thresholds, set parameters for the notifications, and receive notifications when patients' event history matches certain conditions (e.g. rescue event). Additionally, the dashboard 300 can receive and display regular reports of event patterns for specific demographic generated by the respiratory disease analytics system 100.

The dashboard 300 presents a variety of information including tabular data, graphical visualizations, and analyses to users through display "cards" 310. Display cards 310 are conformably suited to smaller displays typical of portable client devices 110, for example mobile phones or tablets, and include "bite size" pieces of information that mimic the simplistic organizational style found in baseball cards. The dashboard 300 may also include a system menu 305 that allows users to navigate through different categories of healthcare information.

Reports provided by the application server 130 are related to the display cards 310. Generally, reports include not only information to be presented to the user through the application 115, but also parameters for specifying which display card 310 is to be used to display the contents of the notification. Any information pushed/pulled from the application server 130 may be associated with one or more cards. For example, a notification can be pushed to the patient based on the outcome of a respiratory disease risk analysis. The dashboard 300 will process the report and determine which card/s to use to present the information in the report. Continuing the example, the recipient of the notification may make a request to pull data from the application server 130. The application server 130 provides the requested data in another notification, and the dashboard 300 then determines which display card 310 to display the requested information.

The dashboard 300 may provide a variety of different display cards 310, which may be organized into categories. An information card type includes cards that display data. Information cards may, for example, display medication rescue events, statistics, and maps including patient data, community data, and regional data. Information cards are further sub-categorized into event, trend, education, and alert display cards. Event cards include data relating to rescue medication events, such as a list of historical medication rescue events for a specific patient, or patient rescue event data overlaid on a geographical map for a specific provider.

Another event card may display an example medication usage report including a map of the location of a rescue usage event, environmental conditions at the location, and an input response area 315 for the recipient to add triggers for the rescue usage event. Another event trend card may display rescue device usage for the previous week including a total number of uses for the time period and a number of uses for each day.

IV. Event-Driven Respiratory Disease Risk Reports

Figure 4:
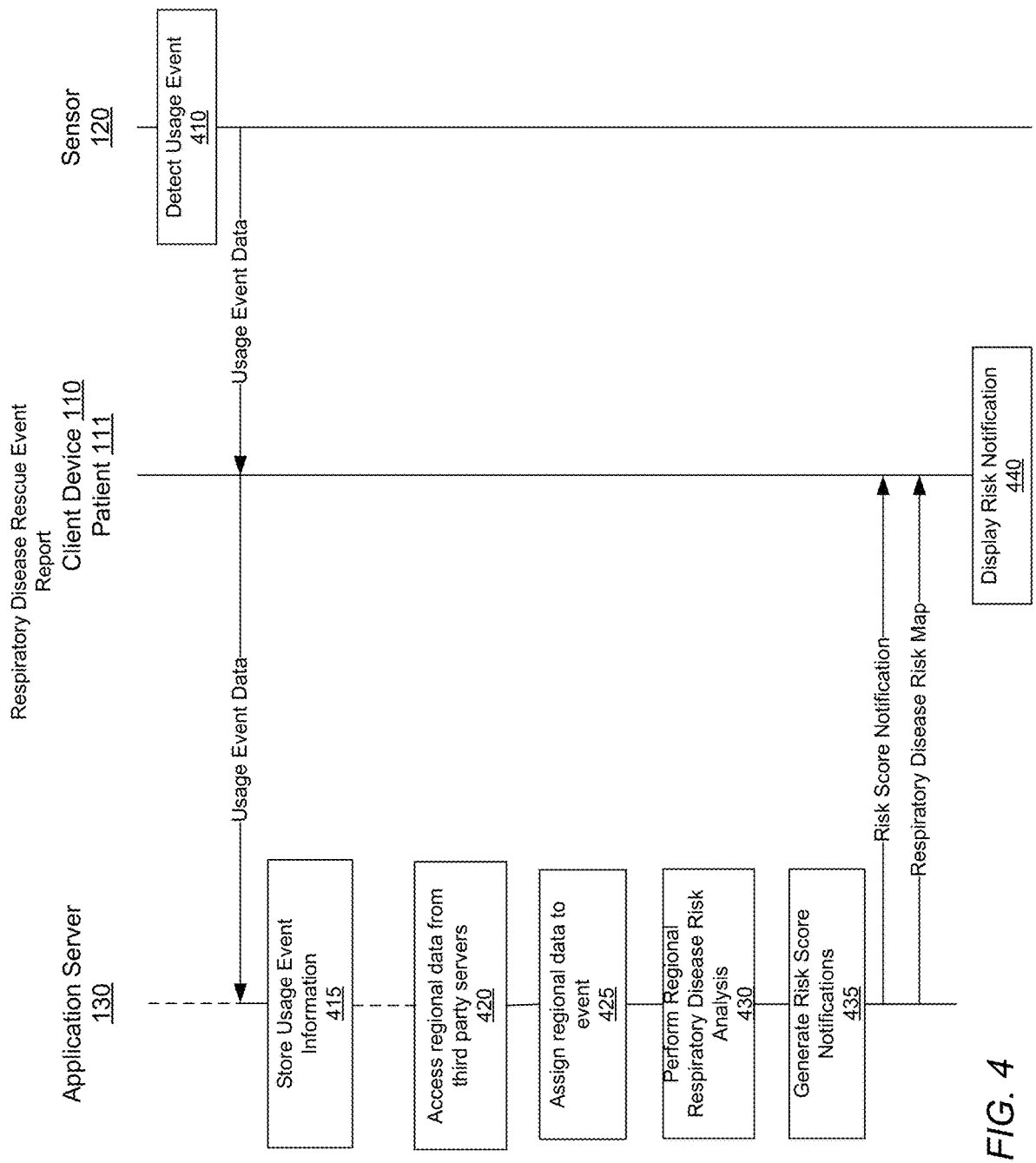
FIG. 4 shows an interaction diagram for providing respiratory disease risk reports based on a location at which a respiratory disease medicament device was used, according to an embodiment

FIG. 4 shows an interaction diagram for providing respiratory disease risk reports based on a location at which a respiratory disease medicament device was used, according to an embodiment. As an initial step, a sensor 120 coupled to a medicament device detects 410 a medicament usage event. As described herein, a medicament usage event refers to any instance during which a patient uses their medicament device to dispense an inhaler treatment, for example applying pressure to a propellant canister to dispense an aerosol treatment. Dispensing of an aerosol treatment may also be referred to as a "puff".

Upon the sensor detecting 410 a rescue usage event, the client device 110 collects and sends usage event data to the application server 130, where the event information is stored 415. Although only on such instance is shown in FIG. 4, this detection and storage process is generally performed with some frequency for a large number of patients, generally upon detection of a rescue usage event. However, this frequency may differ from the frequency at which the analytics system 100 performs risk assessments or the frequency at which the sensor 120 records environmental data describing conditions in a geographic region.

Upon the sensor detecting 410 a rescue usage event, the client device 110 collects and sends the rescue event data to the application server 130, where the event information is stored 415. Although only one such instance is shown in FIG. 4, this detection and storage process is generally performed with some frequency for many patients, generally upon detection of a rescue usage event. However, this frequency may differ from the frequency with which a risk analysis is performed.

The application server 130 may receive manual instructions to accesses 420 stored regional data from one or more said third party servers. In alternate embodiments, the application server 130 may access whatever regional data from third party servers in response to detecting a medicament usage event, whether or not such data has been updated since a most recent medicament usage event. In some embodiments, data may be pulled from third party servers using an external API. As described herein, regional data refers to environmental data, demographic data, and patient health data for a geographic region. Environmental data further refers to air pollutant and weather data for the geographic region. Location demographic data refers population demographics within the geographic region. Patient health data refers to health and health care characteristics describing the population within the geographic region.

The application server 130 assigns 425 the accessed regional data to the detected medicament usage event. As a result, even when stored in the database server 140, each medicament usage event may be recalled with the assigned regional data. The application server 130 performs 430 a regional respiratory disease risk analysis for a time period based on medicament usage events occurring within said time period and the regional data assigned to each event. Based on the respiratory disease risk analysis, the application server generates 435 a risk report which is presented to a patient 111, a medical provider, a third-party entity, or some combination thereof. Therefore, the application server 130 communicates the risk report to a client device 110.

Reports presented to a patient 111 describing the respiratory disease risk analysis may assist in a patient's understanding of a neighborhood or regional level risk. Similarly, reports presented to a provider may alert providers to population-level seasonal changes to allow them to anticipate increased patient visits and concerns. As described herein, a third-party entities may refer to, real estate partners, additional health partners, pharmaceutical or pharmacy/retail companies, hospitals or specialty clinics, asset managers or hedge funds, and federal public health agencies interested in the information obtained from the respiratory disease risk analysis. Pharmacy/retail entities may take such data into account when planning or timing marketing campaigns. Hospitals or clinics may consider such data when planning seasonal staffing and resourcing. Pharmaceutical companies may target medication sales and advertising during certain seasons when respiratory disease-related illnesses are more prevalent. Additionally, urban planning companies and city/county/state/federal urban planning may inform city, state, and federal decision-making around land use, development, transportation, housing, parks, roadways, etc. by evaluating future health risks as a result of land development scenarios or climate change conditions.

In embodiments, in which the application server 130 generates a respiratory disease risk map based on the respiratory disease risk analysis for a geographic region, the application server 130 communicates the respiratory disease risk map to the client device 110. In one embodiment, a respiratory disease risk map describes a risk distribution of multiple environmental conditions throughout the region. In one embodiment, the client device 110 displays 440 the risk report or risk map to a third-party provider, medical provider, or patient 111. The regional respiratory disease risk analysis will be further described with reference to FIG. 6. In some embodiments, the application server 130 may communicate the risk report to a third party, for example a private entity or a city government, which may be distributed, released, or otherwise made available to the users associated with the third party, for example via a website or published report. In such implementations, the application server 130 may communicate the risk report to the third party and the third party may make the risk report publicly available.

Figure 5:
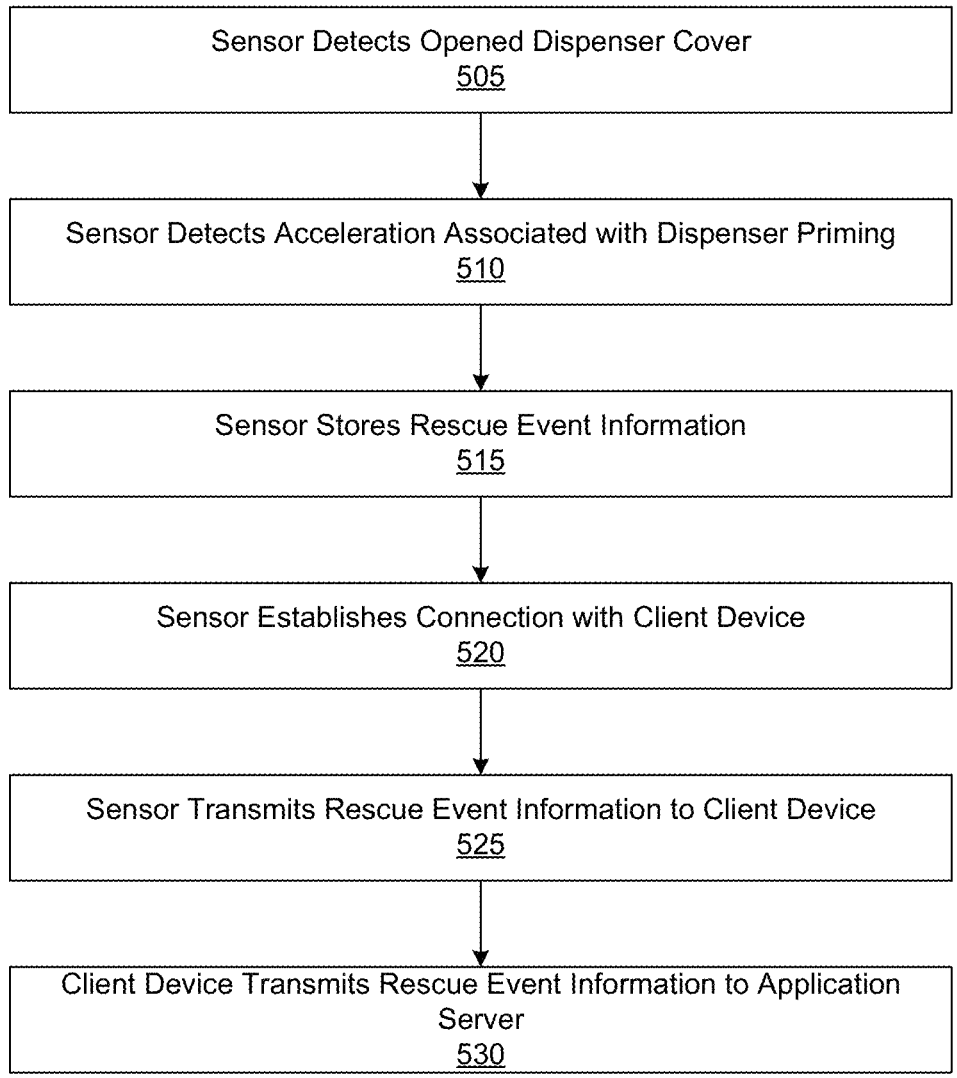
FIG. 5 is a flowchart for detecting a rescue medication event by a respiratory disease analytics system, according to one embodiment.

Referring now to FIG. 5, the application server 130 generally receives a rescue event anytime the patient uses their rescue medicament dispenser 160 to relieve respiratory disease-related event symptoms. As an example of the process for capturing such an event for a particular device 160/sensor 120 combination, at the start of symptoms, the sensor 120 may detect 505 whether a medication dispenser 160 cover is opened. When the medication dispenser cover is opened, the sensor 120 may detect an acceleration 510 associated with a priming of the dispenser 160. For some types of medicament dispensers, the "priming" includes activating a mechanism to release a dose of a medication from a packaging. In other types of medicament dispensers, the "priming" includes a rapid shaking of a medication canister.

After the priming action is detected, the sensor 120 is configured to store 515 data associated with the rescue event in active memory of the sensor 120. The rescue event data may include information that describes the time and date of associated with the rescue event, the status or condition of the medicament device 160 (e.g. battery level), the number of doses of medication remaining (before or after the event), self-test results, and physiological data of a patient being treated with the medicament device 160 as measured by the sensor 120. When the sensor establishes a network connection with either the client device 110 or network 150, the sensor transmits 525 any locally stored rescue event data to the client device 110 or the application server 130. If the event data was transmitted to the client device 110 first, the client device 110 then transmits 530 the rescue event data to the application server 130 when the client device 110 establishes a network connection with the network 150. Depending upon the implementation, either the client device 110 or sensor 120 will add the geographic location where the event took place to the event data transmitted to the application server 130.

V. Regional Respiratory Disease Risk Analysis

V.A Geographic Respiratory Disease Risk Assessments

FIG. 6 is a block diagram illustrating the logical components that carry out the functions of the data analysis module 131, according to one embodiment. In some embodiments, these risk analyses are used to generate reports, for example respiratory disease risk maps, that are sent to a third-party entity, health care provider, or patient in a sufficient timely manner to make the recipient aware of the respiratory disease risk for a given region. In the illustrated embodiment, the data analysis module 131 comprises a historical parameter store 605, a parameter training module 620, an interpolation module 625, an asthma risk module 630, an output normalization module 640, a regional expected usage store 635, and a report module 645. However, in other embodiments, the data analysis module 131 may include different and/or additional components. Similarly, in some cases, functions can be distributed among the components in a different manner than is described here.

In some embodiments, the interpolation module 625 accesses regional data 615 from a third-party server, for example in response to an instruction from an operator. In some instances, a third-party entity, patient, or provider may request a risk assessment at a different level of granularity than that of the accessed regional data 615. For example, a third-party entity may be interested in a census-level assessment rather than a latitude/longitude level assessment. Accordingly, the interpolation module 625 interpolates the regional data 615 to generate interpolated regional data which is received by the respiratory disease risk module 630.

The application server 130 receives an information packet instructing the application server 130 to access data from one or more third-party servers, for example via a Bluetooth connection. In instances in which a connection does not exist and the information packet cannot be communicated to the application server, the packet is stored and resent when a subsequent medicament usage event is detected. In one embodiment, the respiratory disease risk module 630 receives a heartbeat emitted from the sensor 120 at three-hour intervals, unless a medicament usage event has been detected before the conclusion of that three-hour intervals. In such an instance, the respiratory disease risk module 630 receives a heartbeat as a response to the medicament usage event.

In some embodiments, the accessed data is one or more parameters describing a set of conditions, or regional parameters, which the respiratory disease risk module 630 considers when performing a respiratory disease risk analysis. Accordingly, the interpolation module 625 accesses regional data 615 which includes, but is not limited to, air pollutant parameters, weather parameters, demographic parameters, built environment, and regional health parameters. As described herein, values for regional parameters refer to numerical or categorical values which vary between regions over time. Regional data 615 will be discussed in greater detail in Section V.B.

To perform a risk analysis, the respiratory disease risk module 630 implements a mathematical function or another more complex logical structure to determine a metric describing how at risk patients within a geographic region are for suffering from respiratory disease-related incidents. In embodiments in which the respiratory disease risk module 630 generates a risk assessment for a particular patient 111, the respiratory disease risk module 630 additionally receives inputs describing parameters specifically characterizing the patient's condition, for example customized patient health parameters rather than regional health parameters. Additionally, environmental parameters may be accessed for the specific set of latitude/longitude coordinates associated with a patient's client device rather than parameters for an entire geographic region.

For parameters which the respiratory disease risk module 630 receives multiple updated measurements in a single day (e.g., in response to a timed app heartbeat or a rescue event), the respiratory disease risk module 630 may aggregate data to appropriate frequency. The module 630 may implement one or more summary statistic techniques as different inputs for the function to consider. For example, the respiratory disease risk module 630 may determine a mean or median value of the accessed measurements. Alternatively, the respiratory disease risk module 630 may also compute statistically extreme values to consider higher percentile values, for example the $90^{th}$ or $95^{th}$ percentile.

In one embodiment, the respiratory disease risk module 630 outputs an expected number of medicament doses or an average number of doses inhaled by a patient for a geographic region over a specified period of time, for example a single day. Such an output may be representative of an overall respiratory disease risk assessment for a patient in the geographic region given that in conditions associated with a higher respiratory disease risk, a patient may take a larger number of doses compared with conditions associated with a lower respiratory disease risk. Alternatively, the respiratory disease risk module 630 may output an expected number of medicament usage events which would be representative of an overall respiratory disease risk using an approach similar to the description of the expected number of daily medicament use puffs. In other embodiments, the respiratory disease risk module 630 may be trained using a training data assigned binary labels, for example a high risk/low risk classification or 0/1 classification, based on parameters associated with the specific day or a classification indicating whether a computed expected medicament usage exceeds a baseline threshold medicament usage. In such embodiments, the output of the trained function would be a probability value ranging between the binary labels. Although the output of the respiratory disease risk module 630 is described as an expected number of doses inhaled by a patient, one skilled in the art would recognize that the output could be similarly described as any of the alternatives outlined above.

In one embodiment, the interpolation module 625 implements interpolation techniques to interpolate regional data 615 to an area, polygon, or a specific latitude and longitude representative or within a geographic region. For example, regional data 615 may relate to a first geographic region (e.g., Region A), however the interpolation module 625 may be implemented to determine a respiratory disease risk assessment for a second, different geographic region (e.g., Region B). In such an example, the interpolation module 625 implements interpolation techniques to interpolate the regional data 615 describing Region A to generate regional data representative of Region B. The interpolation module 625 uses one or more interpolation techniques, examples of which include, but are not limited to, nearest neighbor searches, linear interpolations (i.e., Delaunay triangulation and linear barycentric interpolation within each triangle), cubic interpolations (i.e., Delaunay triangulation and piecewise cubic Bezier polynomial interpolation within each triangle). In another embodiment, the interpolation module 625 implements Guassian process regression or kriging. In such an embodiment, kernel parameters are fitted using the limited memory, bounded Broyden-Fletcher-Goldfarb-Shanno algorithm to maximize marginal logarithmic likelihood. The choice of hyperparameters (i.e., kernels and error assumptions) may be chosen using random k-fold cross-validation. Candidate kernels include, but are not limited to, constant, radial basis function, Matern, rational quadratic or any combination of these (including repeats). In some embodiments, the specific interpolation method used by the interpolation module 625 depends on the specific use case (i.e., based on one or more of the output, geographic region, or timestamp) and commercial or product requirements.

Depending on the specifications outlined by a patient, provider, or a third-party provider (i.e., an outside air pollutant and weather monitoring entity or a third-party medicament system), the interpolation module 625 may adjust a level of granularity for the interpolation. Levels of granularity range from specific latitude and longitude coordinates to a broader geographic region, for example a zip code. The interpolation module 625 may adjust the granularity to an intermediate level, for example a zip code with an additional four-digit area code defining a smaller geographic area than a standard five-digit zip code or a census tract. In embodiments in which the level of granularity is not a specific set of coordinates, the interpolation is performed to the centroid of the polygon. To initially identify a geographic region at any level of granularity, the interpolation module 625 receives a geographic label, either describing the location of a patient's most recent medicament usage event or describing the most recent location of a patient's inhaler unit. The geographic label may include a set of latitude and longitude coordinates identifying the location of a patient, inhaler unit, medicament usage event, or a combination thereof at a high level of specificity.

The function implemented by the respiratory disease risk module 630 is generated by the parameter training module 620. The parameter training module 620 trains a machine learned model using a training dataset of previously outline environmental, location demographic, or patient health parameters to predict a measure of medicament usage data. Generally, the parameter training module 630 creates a training data set using accessed historical medicament usage data for a region aggregated or segmented on a per day basis, and identifies parameter values for each day. In one embodiment, unlike real-time parameter values received by the respiratory disease risk module 630 which are accessed from third-party servers responsible for recording, for example air pollutant conditions in an area, the parameter training module 620 accesses parameter values assigned to previous instances of medicament usage stored in the historical parameter store 605, for example a prior rescue usage event.

The parameter training module 620 trains the function by identifying how individual parameters of the regional data 615 are related to some measurement of medicament usage events in that region. Accordingly, the parameter training module 620 characterizes the relationship between the event data 610 (the input to the function) of each entry in the training dataset and the expected usage for each event (the label assigned to each entry in the training dataset). Accordingly, as described herein, event data 610 refers to, but may not be limited to, a geographic label identifying the region within which a medicament usage event occurred and a timestamp describing when the medicament usage event occurred. The timestamp assigned to a rescue usage event includes a date and time when the medicament usage event occurred. In some embodiments, event data 610 may be received in response to the conclusion of a time interval or in response to a heartbeat, in addition to medicament usage events. As a result, event data 610 reflects the most accurate geographic and temporal information regarding a patient and their medicament usage device. For medicament usage events where a geographic label is not present, the respiratory disease risk module 630 may retroactively assign a geographic label to the usage event based on any previous medicament usage event which occurred within a 24-hour period (i.e., from 24 hours before to 24 hours after the event in question). For any usage events which still do not have an assigned geographic label, the respiratory disease risk module 630 may assign a patient's home address or an enrollment group location as the geographic label for the event.

As an example, the parameter training module 620 accesses a set of regional parameters including environmental parameters. However, while training the function, the parameter 620 may assign relative weights to each parameter describing the strength of correlation between that parameter and a change in medicament usage events. The parameter training module 620 optimizes the assigned relative weights based on a loss function and iteratively updates the assigned relative weights to improve the accuracy of the function. In embodiments in which the parameter training module 620 is training a linear model or neural network, the module 620 implements variants of gradient descent. Accordingly, the respiratory disease risk module 630 receives, as inputs, parameters from the regional data 615 which have been assigned relative weights indicating a relationship with medicament usage events in the region.

As introduced above, the model is trained using some function or another more complex logical structure. In one embodiment, the parameter training module 620 trains the function using one or more machine learning techniques, examples of which include, but are not limited to, linear (with optional higher-order), logistic, and other forms of regression, decision-tree based models (e.g, random forests and gradient boosting trees), support vector machines, and neural networks (e.g., long short-term memory networks, temporal convolution networks, and transformer networks).

Once a function has been trained based on the training data, the respiratory disease risk module 630, may select the corresponding parameter values from the region parameters 615 to generate a daily expected medicament usage for the region or a probability of a rescue medicament usage event occurring in the region. The determined risk usage is stored by the regional expected usage store 635 and input to the output normalization module 640. Additionally, the output normalization module 640 accesses the expected medicament usages or probability of a medicament usage event computed for one or more regions from the regional expected usage store 635. The output normalization module 640 normalizes the output of the respiratory disease risk module 630 against the outputs computed for one or more geographic regions. In some embodiments, the output normalization module 640 normalizes an output against the outputs determined for geographic regions spread across the country, in addition to any neighboring geographic regions. In one embodiment, the normalization is computed as an overall percentile relative to other geographic regions. In another embodiment, the normalization is computed based on a comparison, for example a difference or ratio, to a centered measurement of the regional output, for example a mean or median.

Based on the normalized output, for example the normalized daily medicament usage for a geographic region, the report module 645 generates a report to be presented to a patient, provider, or a third party entity describing the expected usage for a geographic region. Depending on the recipient, the risk report may include different combinations of information tailored to the interests or insights required by the recipient. Examples of the insights specific to different third-party entities, patients, or medical providers are described above with reference to FIG. 4. In one embodiment, the report contains a map, hereafter referred to as a respiratory disease risk map, with a distribution of expected usages within the geographic region based on the region parameters 615 input to the respiratory disease risk model 630. In some embodiments, a respiratory disease risk map illustrates a risk across a geographic region based on an aggregate of a set of region parameters 615, but in other embodiments, a respiratory disease risk map illustrates a respiratory disease risk across a geographic region based on a single region parameter. In the latter embodiment, a report may include a plurality of respiratory disease risk maps each illustrating a risk distribution across a region based on a single region parameter. Respiratory disease risk maps will be described in greater detail with reference to FIGS. 7A-F.

V.B. Input Parameters

The region parameters incorporated into the risk assessment can be categorized into several groups: air pollutant parameters, weather parameters, local demographic parameters, built environment parameters, and health parameters. Air pollutant parameters and weather parameters may be more broadly categorized as simply "environmental parameters." The numerical values of the parameters are factored into the function generated by the respiratory disease risk module 630 in the form of inputs to the function as described above.

Air pollutant parameters describe measurements for a geographic region including, but not limited to, a concentration of nitrogen dioxide molecules ($NO_2$), a concentration of ozone molecules ($O_3$), a concentration of sulfur dioxide molecules ($SO_2$), a concentration of particulate matter, 2.5 micrometers or less ($PM_{2.5}$), a concentration of particulate matter, 10 microns or less ($PM_{10}$), and a pollen, mold, and spore count. In some embodiments, air pollutant parameter values are accessed periodically from data recovered by the Environmental Protection Agency and other third-party data vendors, for example on an hourly basis. Accordingly, the sensor 120 may receive a heartbeat hourly, prompting the respiratory disease risk analysis module to access updated air pollutant parameter values 615.

Weather parameters describe measurements for a geographic region including, but are not limited to, air temperature, relative humidity, wind speed, wind direction, station pressure, visibility, weather type, dew point, and total precipitation. Similar to the description of air pollutant parameters, weather parameters may be periodically accessed from third party servers, for example the NOAA.

In some embodiments, values for air pollution and weather parameter values, received as input data 615, are assigned to medicament usage events based on the proximity of an air quality monitoring station to the geographic label received as event data 610 for a medicament usage event. If available, air pollutant and weather parameter values are recorded by the closest air quality monitoring station within a state boundary of the geographic region associated with a geographic label assigned to a medicament usage event. If a monitoring station in such a proximity is unavailable, air parameter values are recorded by the closest monitoring station within a climate region of the geographic region associated with a geographic label assigned to a medicament usage event. Air pollution and weather parameter values may be accessed from the closest monitoring station within a one to three-hour window during the same day that the medicament usage event or heartbeat signal were detected.

Built environment parameters describe measurements for a geographic region including, but not limited to, land use type, impervious surface, land surface temperature, greenness (NDVI), tree canopy, property characteristics, and proximity to road networks, periodically accessed from third-party servers such as the United States Geological Survey.

Demographic parameters for a region include, but are not limited to a social vulnerability index (SVI), a composition of the region broken down by race/ethnicity, age, per capita income, average household size, and education level. The SVI is a comprehensive, numerical metric developed by the Center for Disease Control and Prevention which indicates the relative vulnerability of a every census tract in the United States. The SVI ranks each tract based on 15 social factors including unemployment, minority status and disability. Accordingly, when included in region parameters 615, the parameter value assigned to the SVI is the ranking of census tract in which the geographic label is located.

Health parameters for a region include a body mass index (BMI) for the patient or aggregated across a region, a mental and physical health status for the patient or region associated with the medicament usage event, a count of healthy days for the patient associated with the medicament usage, a description of the level of patient access to health care in the region, a level of physical activity associated with the patient or region, and a history of respiratory disease rescue usage events for the patient. Other health parameters may include level of flue prevalence, smoking rate, and obesity rate in the region. When accessed to perform a risk analysis for a geographic region, health parameters describe the health of all patients in the geographic region, for example an average health of all patients in a region.

Demographic parameters and patient health parameters are recorded by the Behavioral Risk Factor Surveillance System (BRFSS), census, and American Community Survey. In some embodiments, the demographic and health parameters are assigned to all medicament usage events experienced by a patient based on the patient's home address. Alternatively, such parameters may be assigned to a medicament usage event based on a geographic label identified from the event data 610.

V.C Respiratory Disease Risk Function

In one embodiment, the respiratory disease risk module 630 implements a linear model to identify the marginal effects of each environmental factor on medicament usage events (e.g., the increase of medicament usage per increase in standard deviation of an individual environmental factor) while maintaining all other environmental factors and confounding variables at a mean parameter value.

For air pollution parameters, the respiratory disease risk module 630 may operate under the assumption that exposure to high concentrations would result in greater detrimental health effects, for example increased respiratory disease risk or increased expected medicament usage. Similarly, the module 630 assumes that exposure to extreme weather conditions would result in a higher or lower number of daily medicament usage events. In a first embodiment, which account for air pollutant and weather parameters, the respiratory disease risk module 630 applies region parameters 615 to the following non-linear quadratic associations by raising the power of each environmental factor predictor to two:

$$\log(Y_{si}) = \beta_0 + \beta_{11} C_{si} + \beta_{12} C_{si}^2 + \gamma_s + \varepsilon_{si} \quad (1)$$

where $\gamma_s$ and $C_{si}$ are respectively, the expected number of medicament usage events and the daily mean environmental exposure for participants in day i. $\beta_0$ is the model constant, $\beta_{11}$ is the linear coefficient of environmental exposure, $\beta_{12}$ is the coefficient of environmental exposure in the squared term, $Y_s$ is the random effect of participants and $\varepsilon_{si}$ is the error term of participants for the day i.

The module 630 assumes the expected medicament usage generated by the function has a Poisson distribution. If there is only a statistically significant linear term in the model for an air pollutant parameter, the module 630 adjusts the direction of association to be positive due to the assumption that exposure to high air pollutant concentrations are associated with greater detrimental health effects. The random effects approach is in appropriate in dealing within individuals, and in processing unbalanced data when there are some subjects with one or just a few observations. R package glmer may be used to handle participants' data through mixed effects modeling techniques.

To evaluate the impacts from possible simultaneous exposures to multiple environmental factors on rescue use, the respiratory disease risk module 630 identifies whether significant multicollinearities exist between the environmental factors through a Variance Inflation Factors (VIF) analysis. The VIF is calculated for each predictor by doing a linear regression of that predictor on all of the other predictors, and then obtaining the variance of the value being explained ($R^2$) from that regression. Literature suggests that a VIF less than 2.5, which corresponds to a $R^2$ value of 0.60, indicates lack of multicollinearity among each other. Therefore, the module 630 added variables for all air pollutant parameter values and at least three weather parameter values into the multi-exposure model described below:

$$\log(Y_{si}) = \beta_0 + \beta_{11} C_{si}^1 + \beta_{12} C_{si}^{1^2} + \ldots + \beta_{j1} C_{si}^j + \beta_{j2} C_{si}^{j^2} + \gamma_s + \varepsilon_{si} \quad (2)$$

where $C_{si}^1$ and $C_{si}^2$ are respectively the levels of exposure to environmental parameter j in linear and squared terms by participants during day i. $\beta_{11}$ and $\beta_{12}$ are the coefficients of the linear and squared terms of environmental parameter j. The coefficients for an individual environmental parameter represent the marginal effect of the environmental factor on the logarithm of medicament usage.

Only those environmental parameters that remained statistically significant in the integrated model were maintained. To further control for the potential confounding of neighborhood and socioeconomic variability, the Social Vulnerability Index (SVI) was added to the model where a higher value indicates a greater vulnerability. The respiratory disease risk module 630 may also control for possible cofounding due to seasonal variability, age and gender, using the function below:

$$\log(Y_{si}) = \beta_0 + \beta_{11}C_{si}^1 + \beta_{12}C_{si}^{1^2} + \ldots + \beta_{j1}C_{si}^j + \beta_{j2}C_{si}^{j^2} + \beta_k V_s + \gamma_s S_i + \beta_p P_s + \varepsilon_{si} \quad (3)$$

where $V_s$ is the overall SVI ranking value assigned to a census tract in which the home address of a patient is located. $S_i$ is the season at day i. $P_s$ represents the health parameters associated with patients in age and gender.

V.D Respiratory Disease Rescue Event Risk Reports

The report module 645 generates a risk report including some combination of informational content for example, a daily expected medicament usage determined by the respiratory disease risk module 630, the interpolated regional data generated by the interpolation module 625, and a respiratory disease risk map generated by the report module 645. As discussed above, the application server 130 generates a risk report for one or more of: a patient 11, a health care provider 112, and/or any other authorized individuals. In some embodiments, a risk report may also be comprised of a recommendation regarding how to prevent future rescue inhaler events based on one or more of the parameters contributing to the medicament usage expectation. In some embodiments, the respiratory disease risk reports are generated and communicated to third-party entities, patients, or health care providers at different frequencies, for example monthly, quarterly, or annually, depending on the requirements or insights requested by the third-party entities.

A respiratory disease risk map may identify one or more census tracts which are at risk for respiratory disease symptoms based on region parameters 615 recorded for those tracts, for example their exposure to air pollutant parameters or weather parameters. In one embodiment, a respiratory disease risk map may be a geographical map of a geographic region describing a distribution of risk measurements (e.g., daily expected medicament usage) across a geographic region. The respiratory disease risk map may be an aggregate risk map for a geographic region during a given period of time. The aggregate risk map comprises a distribution of expected medicament usages within the geographic based on a plurality of parameters assigned to events occurring within that period of time. In alternate implementations, the report may comprise a plurality of aggregate risk maps, each of which illustrates a usage distribution based on an individual parameter within the region.

In some embodiments, respiratory disease risk maps may be updated at varying intervals depending on the type of information which they represent. For example, a risk map presenting a usage distribution based on the census data may be updated when new census data is recorded. In comparison, a risk map generated based on environmental parameters may be updated at the same frequency with which the EPA records updated measurements. In other embodiments, the respiratory disease risk maps may be updated at periodic intervals independent of the frequency with which individual parameters are updated. For example, a risk map based on census data, air pollutant parameters and weather parameters may be updated hourly to reflect updated air pollutant or weather parameters. In such an implementation, parameters which do not update hourly, for example census data, are not updated, but are still included in the updated risk map.

Alternatively, respiratory disease risk maps may illustrate usage distributions for varying periods for time. For example, a risk map, referred to as a "static risk map," may illustrate a usage distribution for a geographic region at a high level of granularity based on data recorded annually or over a multi-year period. As another example, a risk map, referred to as a "seasonal risk map," may illustrate a usage distribution for a geographic region at a high level of granularity based on data recorded monthly.

In some embodiments, the respiratory disease risk module 630 may generate a graph to graphically illustrate the relationship between an individual region parameter and an expected medicament usage for a given day. Accordingly, the respiratory disease risk module 630 may identify at least one inflection point at which the expected medicament usage transitions from being acceptable to a level which qualifies as a condition for a high respiratory disease risk. Accordingly, such inflection points may also be referred to as threshold impact levels. Based on data recorded by monitoring stations, the EPA generates and publishes threshold impact levels for a plurality of parameters. In some embodiments, the risk report module 645 may detect that the threshold impact level determined by the respiratory disease risk module 630 is lower than the threshold impact level published by the EPA for a region. In such instances, the risk report module 645 may generate a report which informs a patient/health care provider of this discrepancy and provides information describing how to prevent a medicament usage event under the lower impact level, a report which informs a third-party provider of the environmental parameters of this discrepancy with a request for the third-party provider to correct their published measurements, or both.

As described above, generally risk reports are delivered through the client device 110 to a third-party entity, a patient, or a provider, however in other embodiments, in the event of improved or worsened conditions, risk reports may be delivered as an SMS report, an email report, a report from an embeddable widget with local respiratory disease conditions, or reports from various IFTTT applets.

VI. Examples

VI.A Example 1

The efficacy and accuracy of the respiratory disease risk analysis module 131 was tested based on environmental parameters, location demographic parameters, and behavioral parameters recorded for Louisville, Kentucky. Louisville, Kentucky ranks among the top 25 most challenging places to live with respiratory diseases in the United States. Louisville, Kentucky is located within Jefferson County.

In an embodiment resembling the above example, the dataset on which the perform of the respiratory disease risk function was tested included 1,020 eligible participants enrolled through clinics, community events, and social media between 2012 and 2016. The participant population included 625 females and 368 males with a mean age of 35 years old with the youngest being three years and the oldest being 90 years. 47.9% participants were Caucasian and 22.6% were African American. For device use, 54.5% participants used Android smartphones, 35.2% used iOS and 10.2% used a wireless hub.

Each participant was equipped with inhaler sensors which tracked the date, time location, and number of medicament usage events for up to 12 months each. Accordingly, the dataset comprises 47,035 unique rescue inhaler usage events and 150,262 sensors heartbeats, or heartbeats indicating non-use. Per guidance from the American Thoracic Society and Europea respiratory Society, a medicament usage event is defined as an SABA actuation occurring within a two-minute time period, although individual doses were also maintained as discrete records in the database for validation purposes. Accordingly, the function may also be trained directly on individual doses rather than medicament usage events. The medicament usage data was merged with over 30 environmental variables at the time and place of occurrence creating a database of more than 5.9 million data points for analysis. The experiment implemented the multi-environmental exposure model of respiratory disease rescue usage described above to control for patient-specific parameters and location demographic parameters recorded during the patient's participation (i.e., socioeconomic status).

As will be described further below, the experiment found air pollutant parameters, for example the concentration of nitrogen dioxide, ozone, and sulfur dioxide, exhibited significant quadratic associations with medicament inhaler use. Similarly, extreme low and high temperatures were associated with increased medicament inhaler use, whereas extreme relative humidity levels were associated with a lower rescue use. Wind speed was also found to exhibit a significant quadratic association.

Air pollutant parameter values were acquired from the EPA's Air Quality System (AQS) for the entire Ohio River Valley Climate region, including the states of Illinois, Missouri, Ohio, West Virginia, Indiana, Kentucky and Tennessee. Air pollutant parameters which were considered included nitrogen dioxide ($NO_2$), ozone ($O_3$), sulfur dioxide ($SO_2$), and particulate matter of 2.5 microns ($PM_{2.5}$) and 10 microns ($PM_{10}$). Each rescue use or heartbeat event was assigned concentrations of the five air pollutant parameters. These parameter assignments may have been derived from multiple monitoring stations because few monitoring sites measure all five pollutants simultaneously. The air pollutant data assignment process occurred in this order, depending on availability: (1) pollutant data assigned from the closest air quality monitoring station, within Kentucky, within the same day; (2) pollutant data assigned from the closest air quality monitoring station, within the Ohio River Valley climate region, within the same day; (3) pollutant data assigned from the closest air quality monitoring station, within Kentucky, within 24 hours of the event; (4) pollutant data assigned from the closest air quality monitoring station, within the Ohio River Valley Climate Region, within 24 hours. Similar to weather data assignments, if no data were matched after the fourth step, the events were removed from analysis (NO2 and 03: 0%; SO2: 8%; PM2.s and PM10: 0.2%). The distance statistics in assigning hourly weather and daily air pollution data to the nearest event data are summarized in the Extended Data Table 2. The median and mean distances from event location (rescue or heartbeat) to linked weather stations were respectively 8.17 km and 8.21 km. The median (mean) matched distances for $NO_2$, $O_3$, $SO_2$, $PM_{2.5}$ and $PM_{10}$ were respectively, 11.91 (47.15) km, 10.44 (22.71) km, 12.50 (13.24) km, 6.93 (8.23) km and 13.07 (29.46) km.

The assigned weather and air pollutant parameters were then aggregated and averaged to daily means and treated as daily environmental exposures for each participant. The daily mean (and standard deviation) air pollutant concentration assignments across the participants for $NO_2$, $O_3$, $SO_2$, $PM_{2.5}$, $PM_{10}$, were respectively, 61.7 (61.7 (17.2) ° F., 6.4 (4.2) m s$^{-1}$ and 65.8 (15.5) percent, for ambient temperature, wind speed and relative humidity.

VI.B Example 2

Figure 7A:
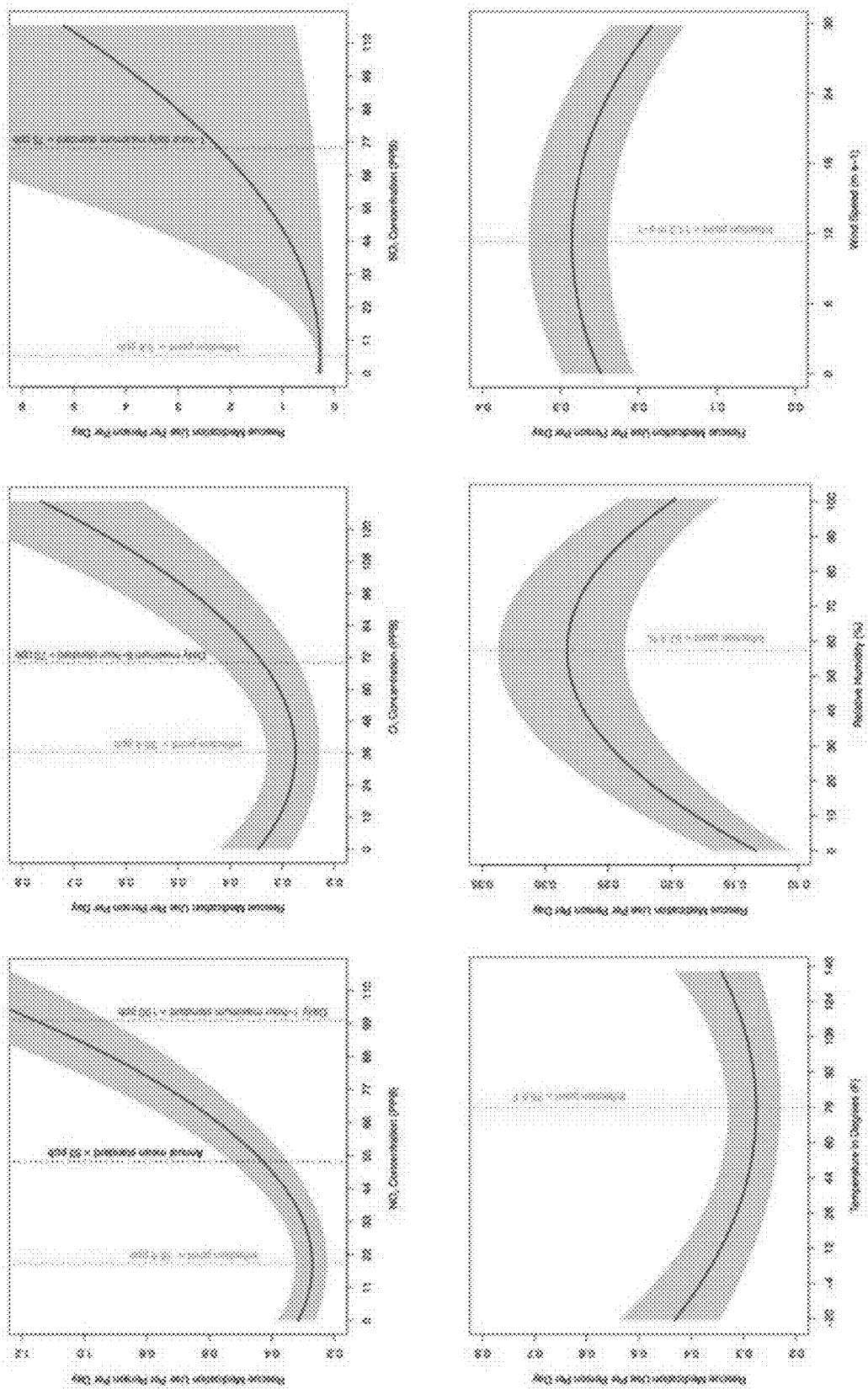
FIG. 7A illustrates the effects of air pollution parameters and weather parameters on medicament usage events, according to an embodiment.

Continuing from the Jefferson County study described above, the quadratic associations of exposure to air pollutants with medicament usage events indicated the existence of thresholds of exposure of each pollutant as illustrated in FIG. 7A. The thresholds consistently occurred below the current National Ambient Air Quality Standards (NAAQS) with some far below the standards. The symptom impact thresholds were 18.9 ppb for $NO_2$ (34.2 ppb below the annual standard of 53 ppb, and 81.2 ppb below the hourly standard of 100 ppb), 36.4 ppb for $O_3$ (33.6 ppb below the annual 8-hour standard of 70 ppb), and 5.8 ppb for $SO_2$ (69.2 ppb below the hourly standard of 75 ppb). These finding demonstrate that air pollution exposure, even at low to moderate levels, may be linked to respiratory disease symptoms, and that current national air pollution standards may not be sufficient to protect human health.

Referring now to FIG. 7A, FIG. 7A illustrates the effects of air pollution parameters and weather parameters on medicament usage events, according to an embodiment. The blue-dotted lines mark the inflection points where the impact of each variable begins to be associated with increased or decreased medicament usage. The black and red dotted lines delineate the air pollutant-specific standard, as noted. The red solid lines represent modeled rescue use per person per day with a 95% confidence interval. The x-axis was transformed per standard deviation increase of a predictor to per original unit increase and the y-axis was also converted from long-transformation to the original scale in medicament usage per person per day. The $O_3$ exposure-response curve showed some increase in medicament usage at lower concentrations. The $NO_2$ exposure-response curve also showed a slight increase in medicament usage at lower concentrations. The curve also showed a slight increase in medicament usage at lower concentrations and may reflect respiratory disease symptoms among more rural participants with low exposure to $NO_2$, but higher exposure to $O_3$. In contrast, there was no increase in medicament usage at low concentrations of $SO_2$. These findings demonstrate that air pollution exposure, even at a low to moderate levels, may be linked to respiratory disease symptoms, and that current national air pollution standards may not be sufficient to protect human health.

Figure 7B:
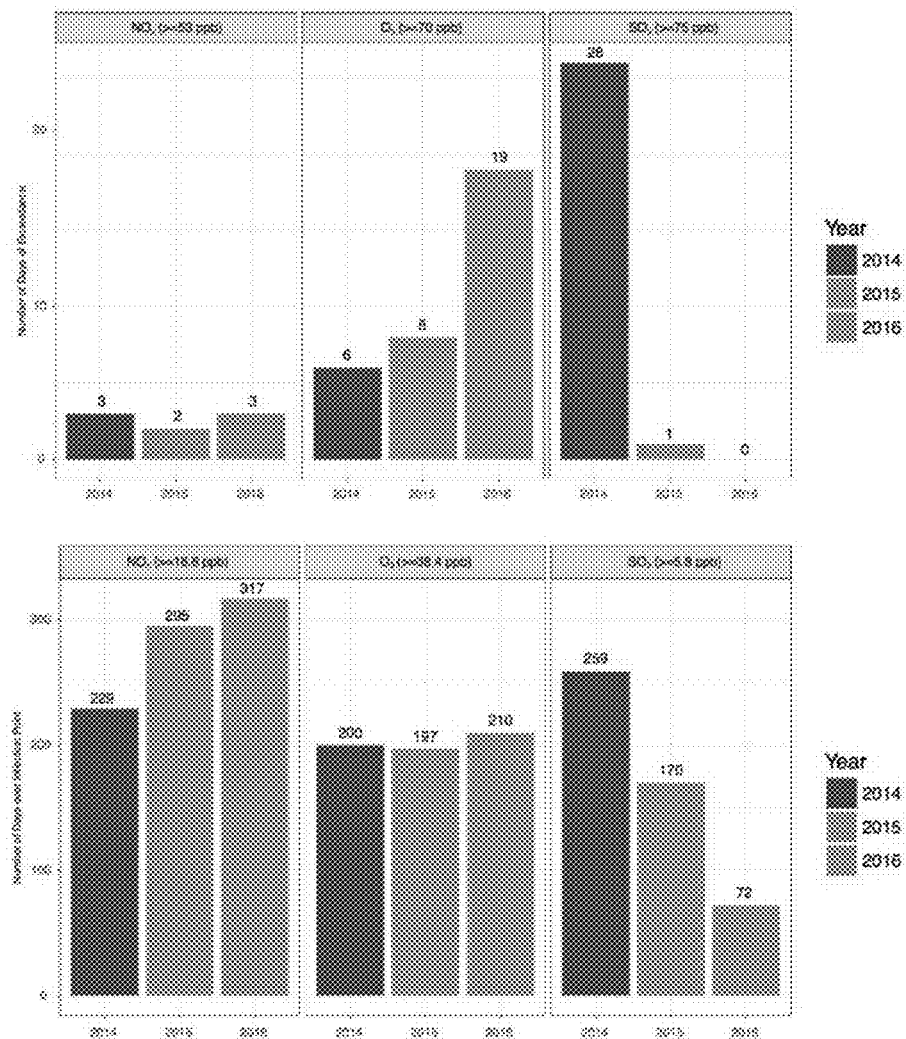
FIG. 7B illustrates the trend of air pollutant parameter concentration exceedances, according to an embodiment.
Figure 7C:
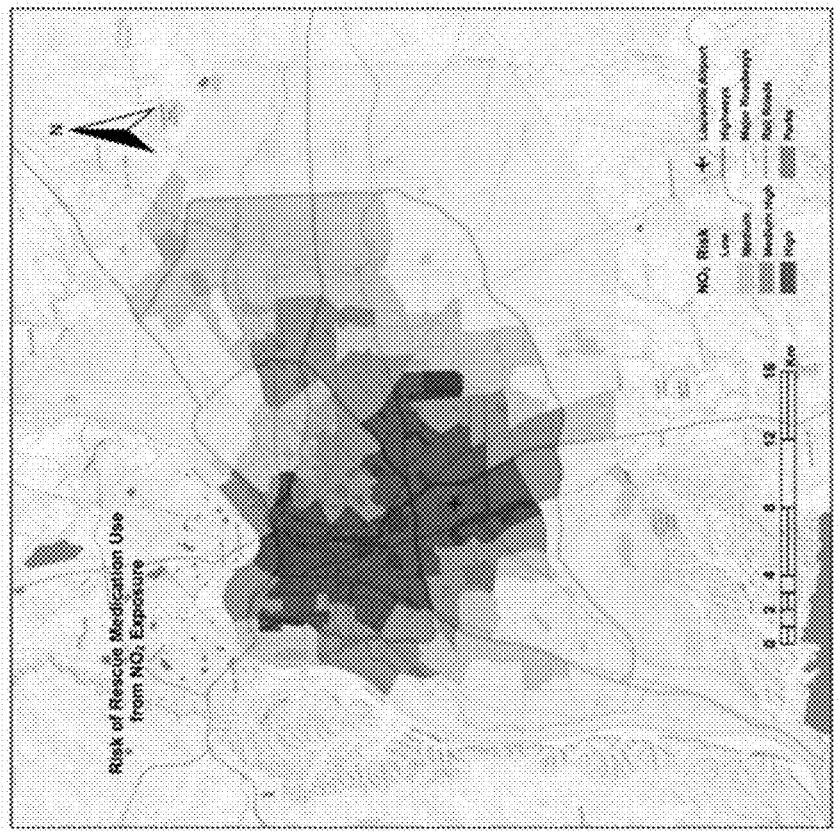
FIG. 7C illustrates the respiratory disease risk estimated at the census tract level due to exposure to $NO_2$, according to an embodiment.
Figure 7D:
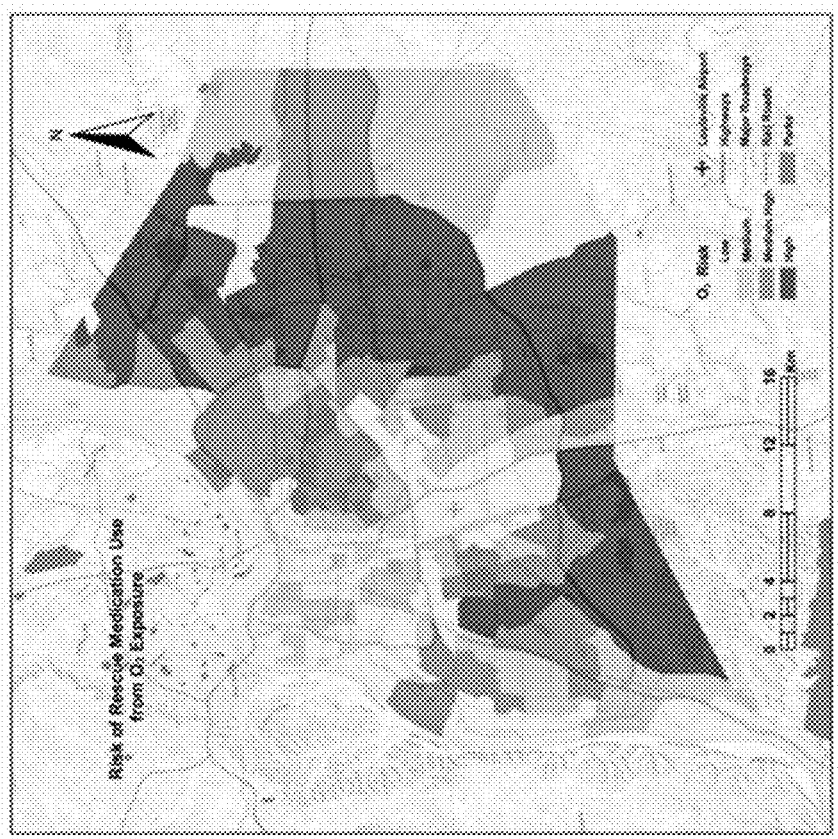
FIG. 7D illustrates the respiratory disease risk estimated at the census tract level due to exposure to $O_3$, according to an embodiment.

Further analysis of air pollution parameters in Jefferson County, identifies the number of days on which air pollutant concentrations exceeded EPA standards from 2014-2016, as well as the number of days during which concentrations exceeded our identified thresholds at which air pollutants had a significant association with medicament usage. FIG. 7B illustrates the trend of air pollutant parameter concentration exceedances, according to an embodiment. Exceedances occurred in Jefferson County between 2014 and 2016 and included those of 1) EPA ambient air quality standards (top panel) and 2) the symptom thresholds identified in this analysis (bottom panel). From 2014-2016, $NO_2$ concentrations exceeded the EPA annual standard (53 ppb) on 8 days (0.7%), but exceeded the symptom threshold (36.4 ppb) on 607 days (55.4%), with a slightly increasing trend. $SO_2$ concentrations exceeded the EPA 1-hour standard (75 ppb) on 27 days (2.5%), but exceeded the symptom threshold (5.8 ppb) 501 days (45.7%), tut that was trend was declining, largely due to improvement at local coal-fired burning power plants.

VI.C Example 3

Figure 7F:
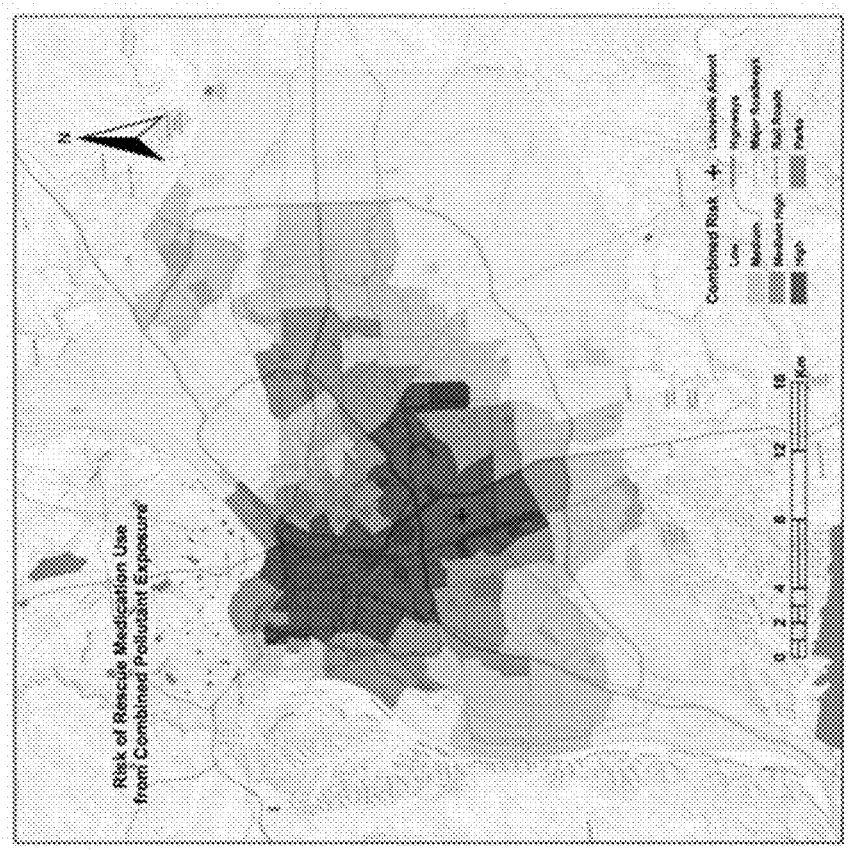
FIG. 7F illustrates the respiratory disease risk estimated at the census tract level due to exposure to $NO_2$, $O_3$, and $SO_2$, according to an embodiment.
Figure 7E:
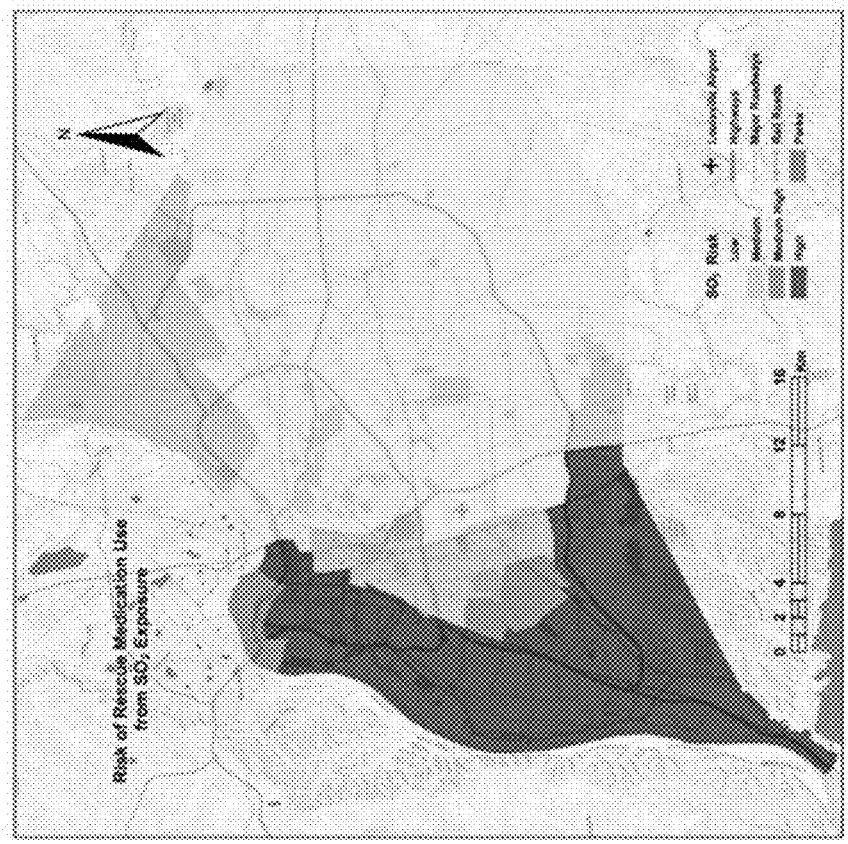
FIG. 7E illustrates the respiratory disease risk estimated at the census tract level due to exposure to $SO_2$, according to an embodiment.
Figure 7G:
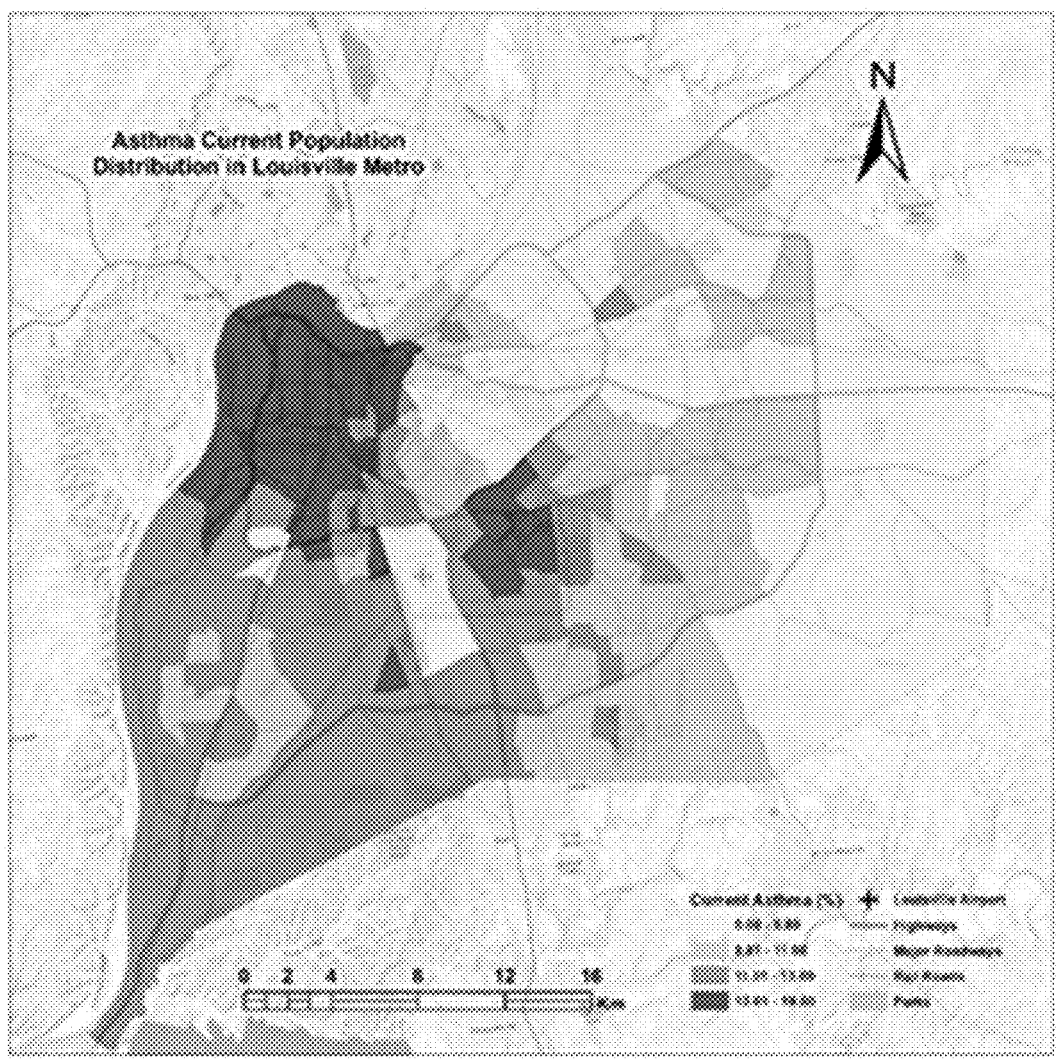
FIG. 7G illustrates the distribution of the respiratory disease population in Jefferson County, Kentucky, according to one embodiment.

Continuing from the Jefferson County study described above, FIGS. 7C-F illustrate the risk of rescue medication use across Jefferson County, according to one embodiment. FIGS. 7C, 7D, 7E, and 7F illustrate the respiratory disease risk estimated at the census tract level due to exposure to $NO_2$, $O_3$, and $SO_2$, and a combination of the three, respectively. The neighborhoods at a highest risk for the combined effects of air pollution parameters were identified in parts of the county associated with exposure to air pollutant parameters and major roadway corridors and industrial activity as illustrated in FIG. 7F. Within those high-risk neighborhoods, lives 23% of the Jefferson County population, and 61 educational facilities (23%), 53 public parks (35%) and 304 churches (39%) are sited. FIG. 7G illustrates the distribution of the respiratory disease population in Jefferson County, Kentucky, according to one embodiment. The illustrated distribution is based on data provided by the CDC 500 cities project.

VI.D Example 4

Continuing from the Jefferson County study described above, the respiratory disease risk module 630 used the mixed-variable function defined in Eq. 3 to perform a respiratory disease risk assessment within each census tract of Jefferson County. The module 630 operates under the assumption that regional mean pollutant concentrations would reach their respective EPA standards, including annual mean of 53 ppb for $NO_2$ and annual 8-hour daily maximum mean of 70 ppb for $O_3$. $SO_2$ concentrations had been declining through the 2014-2016 period and there were no recorded days with $SO_2$ concentration exceeding the national standard of 75 ppb. Therefore, the respiratory disease risk module 630 used the 95 percentile concentrations measured by EPA in the region as the regional mean extreme exposure for the region, which was 23.97 ppb. Assuming that the three criteria pollutants did not have homogeneous distributions across the region, the corresponding EPA standard concentrations were adjusted by the spatial gradients modeled through a machine learning land use regression (LUR) techniques. In building the LUR models, the respiratory disease risk analysis module 130 identified 20 $NO_2$ and 110 $O_3$ regulatory air pollution monitoring stations in the Ohio River Valley that are geographically close and similar to Jefferson County. Additionally, the module 630 included other predictors in the LUR such as land cover types defined by the USGS NLCD (the National Land Cover Database from the United States Geological Survey) (e.g., tree/forests, shrubs, grasslands, high/median/low intensity developments, water body), traffic data provided by HPMS (Highway Performance Management System), canopy distribution and impervious surface composition (by NLCD), elevation, and distance to highways and major roadways. The module 630 also processed Landsat8 data acquired from NASA (National Aeronautics and Space Administration) to derive vegetation greenness (normalized difference vegetation index—NDVI) and surface temperature for the Ohio River.

VI. Benefits

The respiratory disease risk assessment reports for a geographic region convey many benefits to patients 111, providers 112, and even third-party entities. Patients are informed of their risk of a respiratory disease rescue event for a geographic region, and can take action to prevent that occurrence, for example by improving their adherence to their controller medication, staying away from geographic areas with adverse conditions (e.g., air pollution concentrations), or altering their prescribed medication regimen (such as an adjustment of dosage or the introduction of antibiotics or systemic corticosteroids) based on conditions of a geographic region in which they are located. Because the regional data is automatically reported to the application server 130 without the need for patient input, the accuracy and quality of the event data is improved relative to manually-collected data by a health care provider 112 or other entity, and thus the accuracy of the conclusion for the risk of respiratory disease rescue events is also improved.

Additionally, respiratory disease risk assessment reports for a geographic region convey many economic benefits. The economic costs of respiratory disease exacerbations for a day when each air pollutant exceeded its standard, based on historic acute healthcare utilization costs, including emergency department visits and hospitalizations. One day with an $NO_2$ exceedance over 53 ppb, an $O_3$ exceedance over 70 ppb, or an $SO_2$ exceedance over 75 ppb could lead to an additional $90,000, $60,000, or $243,000 of additional acute respiratory disease-related healthcare costs each day, respectively. For example, for all the exceedance days during 2014-2016, the additional acute respiratory disease-related healthcare costs associated with the impact of air pollution exceedances in Jefferson County alone were about $9.5 million, which represents 9.4% of the annual healthcare utilization spend for the county. The incremental indirect costs due to missed work and school because of respiratory disease exacerbations on air pollution exceedance days during 2014-2016 were $3.25 million and $6.56 million, respectively, for a total of $9.81 million.

VII. Additional Considerations

Although the discussion above focuses on respiratory diseases generally, all systems and processes described herein are equally applicable to particular respiratory diseases including, but not limited to, chronic obstructive pulmonary disease (COPD) and chronic respiratory disease (CRD) generally, and consequently can also be used to assist in treatment of COPD and CRD, as well as asthma.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for determining a respiratory disease risk assessment for a first geographic region, the method comprising:
   accessing, from a storage device of a remote server, a set of medicament usage events occurring within the first geographic region during a time period, wherein each medicament usage event of the accessed set of medicament usage events, 1) is detected using an medicament device sensor attached to an inhaler unit that dispenses a medication as part of the medicament usage event, 2) is assigned a time stamp identifying that the medicament usage event occurred during the time period, and 3) is assigned a geographic label identifying that the medicament usage event occurred within the first geographic region;
   identifying, at the remote server, one or more regional parameters that affect medicament usage events in the first geographic region based on the set of medicament usage events occurring within the first geographic region;
   for each medicament usage event of the accessed set of medicament usage events,
      accessing, from the storage device of the remote server, a parameter value recorded during the time period for each of the one or more regional parameters;
      generating a training dataset for training a function to output an expected medicament usage metric for patients in the first geographic region, wherein the training dataset comprises parameter values previously measured for one or more regional parameters;
      training the function by:
         characterizing how each parameter of regional data in the training dataset is related to the expected medicament usage metric in that region, wherein each parameter of the regional data is an input to the function, and wherein the expected medicament usage metric is a label assigned to each entry in the training dataset;
         improving an accuracy of the function by:
            assigning a relative weight to each parameter of regional data, the relative weights describing a relationship between each parameter of regional data and a change in medicament usage events; and
            iteratively updating each assigned relative weight according to a difference between a current output and a target output of the function; and
      implementing the function by inputting into the function the parameter value recorded during the time period for each of the one or more regional parameters;
   accessing, from the storage device of the remote server, an expected medicament usage for patients in a second geographic region during the time period, wherein the second geographic region is different than the first geographic region;
   inputting, at the remote server, the expected medicament usage for patients in the second geographic region into the function to:
      compare the expected medicament usage for patients in the first geographic region to the expected medicament usage for patients in the second geographic region, wherein the second geographic region is different than the first geographic region; and
      normalize the expected medicament usage for patients in the first geographic region based on a comparison of the expected medicament usage for patients in the first geographic region to the expected medicament usage for patients in the second geographic region;
   responsive to the normalization, determining, at the remote server, a risk assessment for the first geographic region based on the expected medicament usage for patients in the first geographic region; and
   sending, from the remote server over a network, a risk report to one or more client devices within the first geographic region, wherein the risk report contains information describing the risk assessment for the first geographic region.

2. The method of claim 1, wherein the time stamp assigned to a medicament usage event identifies a date and time when the medicament usage event occurred.

3. The method of claim 1, wherein the geographic label assigned to a medicament usage event includes a latitude and longitude identifying where the medicament usage event occurred.

4. The method of claim 1, wherein the one or more regional parameters include at least one weather parameter, further comprising:
   air temperature;
   relative humidity;
   wind speed;
   wind direction;
   station pressure;
   visibility;
   weather type;
   dew point; and
   total precipitation.

5. The method of claim 1, wherein the one or more regional parameters include at least one air pollutant parameter, further comprising:
a concentration of nitrogen dioxide molecules ($NO_2$);
a concentration of ozone molecules ($O_3$);
a concentration of sulfur dioxide molecules ($SO_2$);
a concentration of particulate matter, 2.5 micrometers or less ($PM_{2.5}$);
a concentration of particulate matter, 10 microns or less ($PM_{10}$);
a pollen count; and
a mold spore count.

6. The method of claim 1, wherein the one or more regional parameters include at least one location demographic parameter for the first geographic region, further comprising:
a social vulnerability index;
a composition based on race;
an age distribution;
a per capita income;
a household size; and
a level of education.

7. The method of claim 1, wherein the one or more regional parameters include at least one health parameter, further comprising:
a level of flu prevalence for the region;
a smoking rate for the region;
an obesity rate for the region;
a body mass index for the region associated with a medicament usage event;
a health status for the region associated with the medicament usage event;
a count of healthy days for the region associated with the medicament usage event;
a description of the level of regional access to health care;
a level of physical activity associated with the region; and
a history of respiratory disease medicament usage events for the region.

8. The method of claim 1, further comprising:
accessing parameter values for one or more air pollutant parameters, weather parameters, demographic parameters, location demographic parameters, and health parameters recorded for the first geographic region during a previous time period;
inputting the parameter values for the one or more air pollutant parameters, weather parameters, demographic parameters, location demographic parameters, and health parameters recorded for the first geographic region during the previous time period to the function to generate an output describing an effect of each of the one or more regional parameters on the expected medicament usage for the first geographic region; and
selecting a subset of input air pollutant parameters, weather parameters, demographic parameters, location demographic parameters, and health parameters to input to the function based on outputs generated by the function.

9. The method of claim 8, further comprising:
accessing a training dataset comprising parameter values for one or more air pollutant parameters, weather parameters, demographic parameters, location demographic parameters, and health parameters recorded for a plurality of previous time periods; and
for each previous time period of the plurality of previous time periods, training the function to output a metric describing the effect of each parameter on the expected medicament usage for patients in a geographic region.

10. The method of claim 1, further comprising:
assigning parameter values for air pollutant parameters of the one or more regional parameters to each medicament usage event of the accessed set of medicament usage events by identifying an air quality monitoring station within a boundary of the first geographic region; or
assigning parameter values for air pollutant parameters of the one or more regional parameters to each medicament usage event of the accessed set of medicament usage event by identifying an air quality monitoring station within a climate region of the first geographic region.

11. The method of claim 1, further comprising:
assigning parameter values for air pollutant parameters of the one or more regional parameters to each medicament usage event of the accessed set of medicament usage events based on the time stamp assigned to the medicament usage event; or
assigning parameter values for air pollutant parameters of the one or more regional parameters to each medicament usage event of the accessed set of medicament usage events such that the parameter values were recorded within 24 hours of the time stamp assigned to the medicament usage event.

12. The method of claim 1, further comprising:
assigning parameter values for location demographic parameters of the one or more regional parameters to each medicament usage event of the accessed set of medicament usage events such that the parameter values were recorded within at least a year of the time stamp assigned to the medicament usage event; and
assigning parameter values for behavioral parameters of the one or more regional parameters to each medicament usage event of the accessed set of medicament usage events such that the parameter values were recorded within at least a year of the time stamp assigned to the medicament usage event.

13. The method of claim 1, further comprising:
determining a set of representative parameter values recorded during for a previous time period based on parameter values assigned to medicament usage events occurring within the previous time period; and
inputting the representative parameter values into the function to determine an expected medicament usage for the first geographic region during the time period.

14. The method of claim 13, further comprising:
determining the set of representative parameter values by averaging parameter values for each air pollutant parameter of the one or more regional parameters and parameter values for each weather parameter of the one or more regional parameters.

15. The method of claim 1, further comprising:
accessing, from a third-party server, parameter values recorded for one or more geographic regions during the time period;
accessing the geographic label assigned to each medicament usage event of the set of medicament usage events;
interpolating the parameter values accessed from the third-party server to generate regional parameter values for the first geographic region identified by the geographic label; and
assigning the regional parameter values to each medicament usage event of the set of medicament usage events based on the time stamp assigned to the medicament usage event.

16. The method of claim 1, wherein the function determines one of the following:
   an expected number of medicament usage events for the time period; or
   a probability of a medicament usage event occurring during the time period.

17. The method of claim 1, wherein the function implements one or more interpolation techniques to determine the expected medicament usage for patients in the first geographic region during the time period.

18. The method of claim 1, wherein adjusting the expected medicament usage for patients in the first geographic region comprises:
   comparing the expected medicament usage for patients in the first geographic region to the expected medicament usage for patients in the second geographic region; and
   normalizing the expected medicament usage for patients in the first geographic region based on the comparison.

19. The method of claim 1, wherein adjusting the expected medicament usage for patients in the first geographic region comprises:
   comparing the expected medicament usage for patients in the first geographic region to an expected medicament usage determined for each of one or more geographic regions that are different than the first geographic region; and
   normalizing the expected medicament usage for patients in the first geographic region based on the comparison.

20. The method of claim 1, further comprising:
   for an air pollutant parameter of the one or more regional parameters, determining a relationship between a measurement for the air pollutant parameter in the first geographic region and the expected medicament usage for the first geographic region; and
   identifying, based on the relationship, one or more inflection points at which the expected medicament usage for the first geographic region increased based on a change in the measurement for the air pollutant parameter in the first geographic region.

21. The method of claim 20, further comprising:
   accessing, from a third-party database, a threshold concentration of the air pollutant parameter;
   comparing an inflection point of the one or more inflection points to the threshold concentration of the air pollutant parameter; and
   responsive to determining that the inflection point is below the threshold concentration of the air pollutant parameter, sending a report to a host of the third-party database to update the threshold concentration of the air pollutant parameter.

22. The method of claim 1, wherein the risk report comprises informational content regarding the expected medicament usage for patients in the first geographic region, a subset of the one or more regional parameters responsible for a change in the risk assessment for the first geographic region compared to a previous time period.

23. The method of claim 22, wherein the risk report further comprises informational content regarding the expected medicament usage for patients in the first geographic region, a recommendation regarding how to prevent future medicament usage events while a patient is located within the first geographic region, the recommendation based on the subset of the one or more regional parameters responsible for the change in the risk assessment for the first geographic region.

24. The method of claim 1, wherein the risk report further comprises an aggregate risk map for the first geographic region during the time period, wherein the aggregate risk map further comprises a distribution of risk assessments within the first geographic region based on one or more parameter values recorded during the time period.

25. The method of claim 1, wherein the risk report further comprises a plurality of parameter risk maps for the first geographic region during the time period, wherein each parameter risk map of the plurality of parameter risk maps comprises a distribution of risk assessments within the first geographic region based on individual parameter values recorded for the first geographic region during the time period.

26. A non-transitory computer readable storage medium comprising computer program instructions for determining a respiratory disease risk assessment for a first geographic region that when executed by a computer processor cause the computer processor to:
   access, from a storage device of a remote server, a set of medicament usage events occurring within the first geographic region during a time period, wherein each medicament usage event of the accessed set of medicament usage events, 1) is detected using an medicament device sensor attached to an inhaler unit that dispenses a medication as part of the medicament usage event, 2) is assigned a time stamp identifying that the medicament usage event occurred during the time period and, 3) is assigned a geographic label identifying that the medicament usage event occurred within the first geographic region;
   identify, at the remote server, one or more regional parameters that affect medicament usage events in the first geographic region based on the set of medicament usage events occurring within the first geographic region;
   for each medicament usage event of the accessed set of medicament usage events,
      access, from the storage device of the remote server, a parameter value recorded during the time period for each of the one or more regional parameters;
   generate a training dataset for training a function to output an expected medicament usage metric for patients in the first geographic region, wherein the training dataset comprises parameter values previously measured for one or more regional parameters;
   train the function by:
      characterizing how each parameter of regional data in the training dataset is related to the expected medicament usage metric in that region, wherein each parameter of the regional data is an input to the function, and wherein the expected medicament usage metric is a label assigned to each entry in the training dataset;
      improving an accuracy of the function by:
         assigning a relative weight to each parameter of regional data, the relative weights describing a relationship between each parameter of regional data and a change in medicament usage events; and
         iteratively updating each assigned relative weight according to a difference between a current output and a target output of the function; and
   implement the function by inputting into the function the parameter value recorded during the time period for each of the one or more regional parameters; and
   access, from the storage device of the remote server, an expected medicament usage for patients in a second geographic region during the time period, wherein the second geographic region is different than the first geographic region;

input, at the remote server, the expected medicament usage for patients in the second geographic region into the function to:

compare the expected medicament usage for patients in the first geographic region to the expected medicament usage for patients in the second geographic region, wherein the second geographic region is different than the first geographic region; and normalize the expected medicament usage for patients in the first geographic region based on a comparison of the expected medicament usage for patients in the first geographic region to the expected medicament usage for patients in the second geographic region;

responsive to the normalization, determine, at the remote server, a risk assessment for the first geographic region based on the expected medicament usage for patients in the first geographic region; and send, from the remote server over a network, a risk report to one or more client devices within the first geographic region, wherein the risk report contains information describing the risk assessment for the first geographic region.

27. A system comprising:

a processor; and a non-transitory computer readable storage medium comprising computer program instructions for determining a respiratory disease risk assessment for a first geographic region that when executed by a computer processor cause the processor to:

access, from a storage device of a remote server, a set of medicament usage events occurring within the first geographic region during a time period, wherein each medicament usage event of the accessed set of medicament usage events 1) is detected using an medicament device sensor attached to an inhaler unit that dispenses a medication as part of the medicament usage event 2) is assigned a time stamp identifying that the medicament usage event occurred during the time period and 3) is assigned a geographic label identifying that the medicament usage event occurred within the first geographic region;

identify, at the remote server, one or more regional parameters that affect medicament usage events in the first geographic region based on the set of medicament usage events occurring within the first geographic region;

for each medicament usage event of the accessed set of medicament usage events, access, from the storage device of the remote server, a parameter value recorded during the time period for each of the one or more regional parameters;

generate a training dataset for training a function to output an expected medicament usage metric for patients in the first geographic region, wherein the training dataset comprises parameter values previously measured for one or more regional parameters;

train the function by:

characterizing how each parameter of regional data in the training dataset is related to the expected medicament usage metric in that region, wherein each parameter of the regional data is an input to the function, and wherein the expected medicament usage metric is a label assigned to each entry in the training dataset;

improving an accuracy of the function by:

assigning a relative weight to each parameter of regional data, the relative weights describing a relationship between each parameter of regional data and a change in medicament usage events; and iteratively updating each assigned relative weight according to a difference between a current output and a target output of the function; and implement the function by inputting into the function the parameter value recorded during the time period for each of the one or more regional parameters;

access, from the storage device of the remote server, an expected medicament usage for patients in a second geographic region during the time period, wherein the second geographic region is different than the first geographic region;

input, at the remote server, the expected medicament usage for patients in the second geographic region into the function to:

compare the expected medicament usage for patients in the first geographic region to the expected medicament usage for patients in the second geographic region, wherein the second geographic region is different than the first geographic region; and normalize the expected medicament usage for patients in the first geographic region based on a comparison of the expected medicament usage for patients in the first geographic region to the expected medicament usage for patients in the second geographic region;

responsive to the normalization, determine, at the remote server, a risk assessment for the first geographic region based on the expected medicament usage for patients in the first geographic region; and send, from the remote server over a network, a risk report to one or more client devices within the first geographic region, wherein the risk report contains information describing the risk assessment for the first geographic region.

* * * * *